United States Patent
Dixon et al.

(12)

(10) Patent No.: US 6,316,697 B1
(45) Date of Patent: Nov. 13, 2001

(54) CONSTITUTIVE DISEASE RESISTANCE (CDR1) GENE AND METHODS OF USE THEREOF

(75) Inventors: Richard A. Dixon, Ardmore, OK (US); Yiji Xia, San Diego, CA (US); Christopher Lamb, Norwich (GB)

(73) Assignees: Noble Foundation Inc., Ardmore, OK (US); The Salk Institute for Biological Studies, La Jolla, CA (US)

( * ) Notice: Subject to any disclaimer, the term of this patent is extended or adjusted under 35 U.S.C. 154(b) by 0 days.

(21) Appl. No.: 09/353,332

(22) Filed: Jul. 14, 1999

Related U.S. Application Data

(60) Provisional application No. 60/092,696, filed on Jul. 14, 1998.

(51) Int. Cl.[7] .............................. C12N 5/04; C12N 15/09; C12N 15/29; C12N 15/82; A01H 5/00
(52) U.S. Cl. ..................... 800/279; 800/295; 800/287; 800/278; 435/69.1; 435/320.1; 435/252.2; 435/468; 435/419; 536/23.1; 536/23.6; 536/24.1
(58) Field of Search ..................................... 800/279, 295, 800/297, 278; 435/69.1, 320.1, 252.2, 468, 419; 536/23.1, 23.6, 24.1

(56) References Cited

FOREIGN PATENT DOCUMENTS

WO 94/16077   7/1994   (WO) .
WO 95/02319   1/1995   (WO) .

OTHER PUBLICATIONS

Dixon et al., "Metabolic engineering: prospects for crop improvement through the genetic manipulation of phenylpropanoid biosynthesis and defense responses—a review," *Gene*, 179:61–71 (1996).

Dixon et al., "Engineering Disease Resistance in Plants: An Overview," *Molecular Methods in Plant Pathology*, Sing, Rudra P. et al. (eds). pp. 249–270 (1995).

*Primary Examiner*—Phuong T. Bui
*Assistant Examiner*—Medina A. Ibrahim
(74) *Attorney, Agent, or Firm*—Knobbe, Martins, Olson & Bear LLP

(57) ABSTRACT

Substantially purified CDR1 polypeptide, isolated polynucleotides encoding CDR1 polypeptide, vectors containing CDR1, host cells expressing CDR1, and antibodies which bind to CDR1 are all provided. The invention also provides a method of producing a genetically modified plant characterized as having increased disease resistance as compared to wild-type plants. A method is also provided for identifying novel disease resistance genes by probing a nucleic acid library with at least a fragment of a polynucleotide encoding CDR1, and selecting those clones that hybridize with the fragment.

26 Claims, 6 Drawing Sheets

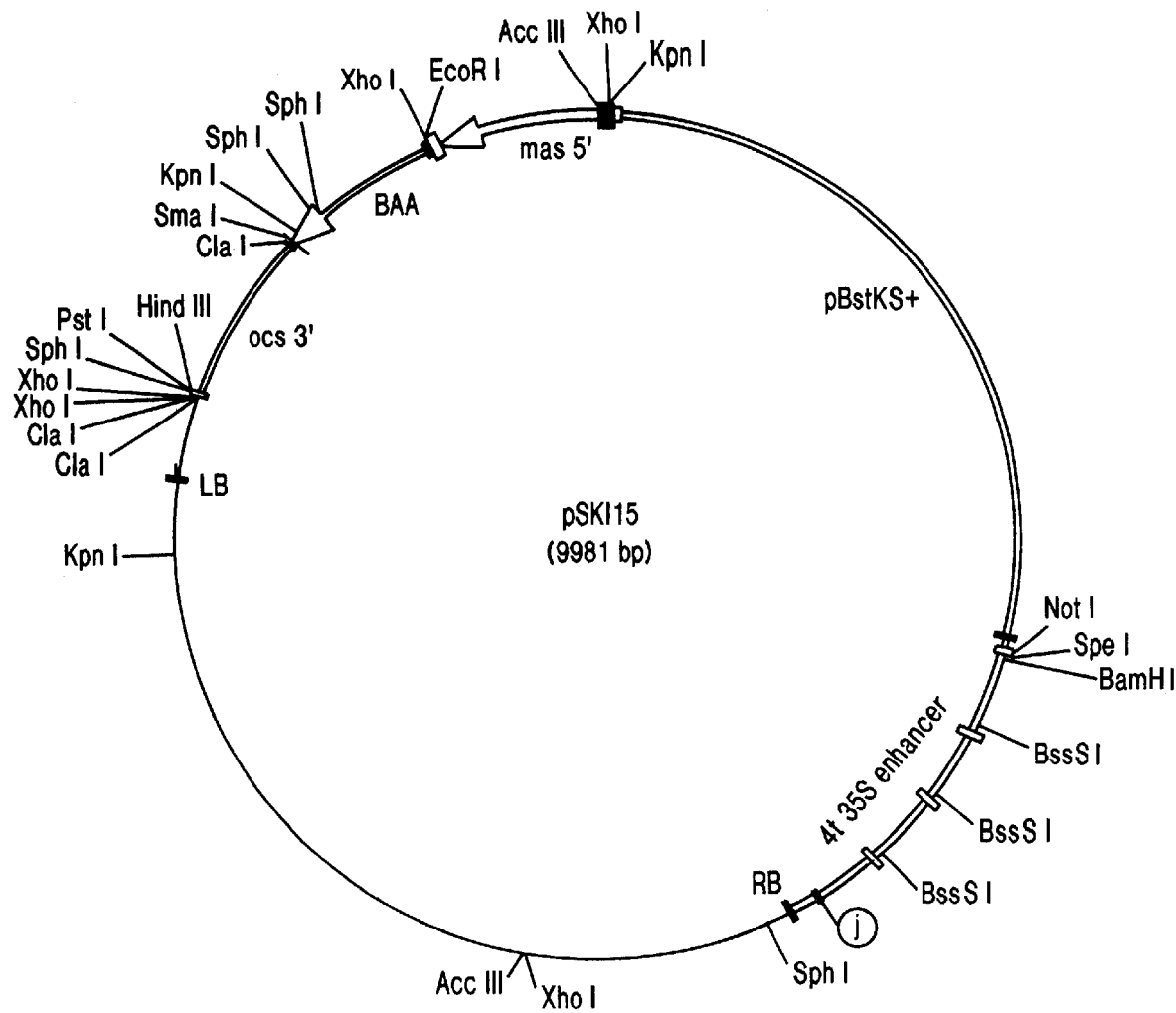
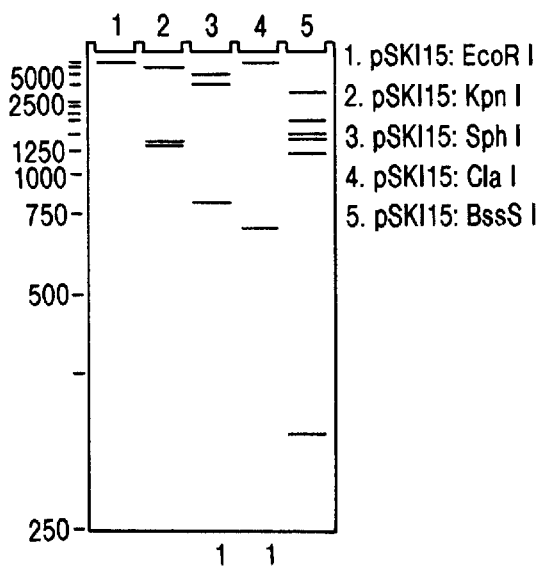
FIG. 1

FIG. 3A

Deduced amino acid sequence (SEQ ID NO:2)

MASLFSSVLLSLCLLSSLFLSNANAKPKLGFTADLIHRDSPKSPFYNPMETSSQRLRNAIHRSVNRVFHFTEKDNTPQPQ
IDLTSNSGEYLMNVSIGTPFFPIMAIADTGSDLLWTQCAPCDDCYTQVDPLFDPKTSSTYKDVSCSSSQCTALENQASCS
TNDNTCSYSLSYGDNSYTKGNIAVDTLTLGSSDTRPMQLKNIIIGCGHNNAGTFNKKGSGIVGLGGPVSLIKQLGDSID
GKFSYCLVPLTSKKDQTSKINFGTNAIVSGSGVVSTPLIAKASQETFYYLTLKSISVGSKQIQYSGSDSESSEGNIIDS
GTTLILLPTEFYSELEDAVASSIDAEKKQDPQSGLSLCYSATGDLKVPVITMHFDGADVKLDSSNAFVQVSKDLVCFAFR
GSPSFSIYGNVAQMNFLVGYDTVSKTVSFKPTDCAKM genomic DNA for CDR1 (SEQ ID NO:1)

```
GGACATTCTT GGTCTACTCC AAGAATATCA AAGATCCAGT CTCAGAAGAC CAGAGGGCTA TTGAGACTTT
TCAACAAAGG GTAATATCGG GAAACCTCCT CGGATTCCAT TGCCCAGCTA TCTGTCACTT CATCGAAAGG
ACAGTAGAAA AGGAAGATGG CTTCTACAAA TGCCATCATT GCGATAAAGG AAGGCTATC GTTCAAGATG
CCTCTACCGA CAGTGGTCCC AAAGATGGAC CCCCACCCAC GAGGAACATC GTGGAAAAAG AAGACGTTCC
AACCACGTCT TCAAGCAAG TGGATTGATG TGATATCAAA TTATTTTATT TTAATTGTAC
TATATTTATA TGTGATGTT TCTCTTAAAT AAATATGAATA TGACTATATA TATAGGTAC
TATATATATA ATTATTTCA AACGATTCTC TGTCAATTTC TTGATATTTT TAACTAAAA TCCATTTTT
TGATCTTCAA CTGATTAAC AAACATTAAA CCTAAAGTCA CACATGTAT TTCTGTACAT GCCACGGATC GAAAATGAGT
AAAAATAGA ATATTTTTA GAATCCTTAT ATTACGAAAA TATCCGGTTA CATTCGTTGA ATACTTTAAT AAATGATACA GACCAAAATT
CAGTAAATGA GAATATCAA AAGAAGAAG AAAATATGTA AGCATTAGA AATAAAATAA CTTGGAGATA GAAGAATCTA
AGAGAACAA CCATATGAAT GAATGGTACA CTCCCTCGTAA ATAAAATAAT ATATGCATCA TAAGCAAACC AAATGAGAAA
ATAAACACGT TTATTATTC TTAATACGTC AGATTCCTG AACACAAAT GATATAATTT GTAGATAACT
ATCTTCACTT GTAAGAACTC ACTATCTATT ATCATTTAT AACCACCATC TCATTAATCT TATAAATATG
TACTCAAAAC ATTGTCAAAA ATTATATGTA GTAAACACT TTAAACTACA AATCAAAACA ATGCCTCTC
TATTCATTAG TCTCCTTG AGTTCTCTTC ACTTTTCTC ACTTTTCTC TCAAATGCAA ACGCTAAGCC
```

```
AAAACTAGGC TTCACCGCGG ATCTAATCCA CCGTGATTCT CCTAAATCGC CGTTCTATAA CCCGATGGAA
ACCTCTTCCC AGGGTCTACG AAACGCGATC CACCGATCCG TTAACCGTGT TTTCCATTTC ACTGAAAGG
ATAACACACC ACAACCACAG ATTGACCTCA CCTCAAATAG CGGTGAATAT CTCATGAACG TATCCATTGG
AACACCTCCT TCCCGATCA TGGCCATGCA CGACACCGGA AGTGATCTCC TCTGGACGCA GTGGCACCA
TGCGATGATT GTTACACTCA AGTTGATCCT CTCTTTGACC CTAAAACGTC TTCCACATAC AAAGACGTTT
CTTGCTCCTC AAGTCAATGT ACTGCCCTAG AAAATCAAGC CTCTTGTTC ACAAATGACA ACACTGTTC
TTACTCATTG TCTTACGGGG ATAACTCATA CACAAAGGGT AACATCGCCG TGGATACCTT AACGCTCGGC
TCCAGCGATA CCCGCCCTAT GCAGCTTAAG AATATTATTA TCGGTGTGG TCACAACAAC GCTGGAACGT
TTAACAAGAA AGGCTCTGAA ATCGTCGGAC TAGGTGGTGG TCCGGTTTCG CTTATCAAGC AACTTGGCGA
CTCCATCGAC GGTAAATTCT CATACTGCTT ACTTCCAAA AGGATCAAAC GAGTAAAATC
AACTTCGGAA CCAATGCCAT CGTGTCGGGA GGTTCCTCTA TCTCAACTCC TCTGATCGCA AAGGGTCTC
AAGAGACCTT CTATTACCTA ACCCTAAAT TCAGGAGTTG CCATTAGCGT GGGAAGCAAG CAAATCCAAT ACTCAGGCTC
AGATTCTGAA AGCAGCGAGG GAAACATCAT CATCGATTAT GGCACAACTT TAACGTTATT ACCGACTGAA
TTTTACTCCG AGCTCGAGGA TGCGGTTGCA TCCTCTATCG GAAGCAAGAT ACTATGCATT CCACAAAGCG
GTTGAGTCT ATGTTACAGT GCAACCGGAG ATCTAAAAGT TCCAGTCATT TGGTTTGCTT TTGATGGAGC
CGATGTGAAG CTTGACTCCT CCAATGCCTT TGTACAAGTC TCGGAGGATT TGGTTGGATAC TGCCTTCCGC
GGAAGCCCGA GTTTCTCCAT ATACGGTAAT GTGGCGCAGA TGAACTTTCT TGTTGGATAC GACACTGTTT
CCAAAACGGT GTCATTTAAG CCAACAGATT GTGCAAAGAT GTAGTTGTTT CATCTCAACA TGTTTTCAA
AATTGTGTTT TCAATTACAA TAATGCTGA TTTAGTTTCA GCCTTAGTC TTTTGAATTT TCTAATTCA
CATGTAGTAG TCTATCTTTT CAAGGGAGAG TTAAATTCTC GACCTTTTGT TCTTTGGTG ATGCTTTGTA
TTTCCTTGAA TTTTTTCATT CAATTAAAT CATGAAAACC TTATCTCCGG TAACTATTTT CTTGTCCATC
TCTATACTCT ATATCTTTT ATAAGAAACA ATCTAGAAAT AACCAAATAT GACAAGACAA TTCTATAATT
TTGTTCAAA TTTAGTTTT GATGAATGTG ATTCTAATTC ATTCTATATC AATATTGCTT TGTCATTAT
ATTATTGTGA TACTATTCTA TTTGATGTG TTCTATATTT ATAAATAATT CAATTAGTTT CAATTAGCT AATGGATTA TGGGATTA
AATATTTG TACTATTCTA AAATATTTAT ATAATAAAAT ATAATAATT CAATTAGTTT TCTTCTTAA TCTCTTATAT
AAATATAAAT ATATCTTATA AGAAATAAAT ATATTTTATA AATTTAGATC ATGAATCATA AAAATCCAGC TGTAGATAAA CATAACAAGG
AGGTGGATGA TACATGGCCT AATTAGATCA ATGAATCATA
```

FIG. 3B

```
ATGAATGGTA CAATCCTGGT CAAAAAAAAT AAAAGGAAAA GTTATATGCA TTAAAATGAG AAAATCTTCG
CTTTTATTGT TTCTTATTTA TCAGATTCTC TAAATGTAAA TGACACAATT TGTAGATAAT TTACTAAAAA
TGTAAGAATC TCATCATGTA CTACCATTTA TGAATCCTTA CCAATTGAC CTTATAAATA TTACTCATCA
GATTGTCAAA AGTAAAAACT GACCATTCAG GCAATCACTT AACTACAAAT CTAAGAAAAT GGCCTCTCTA
TTCACTTCAC TCTCCTTGTC TCTATGTTTA TTCTCTCTC CTATTTTCTC AAACGCAAAC GCCAAACCAA
AACTAGGCTT CACCGCGGAT CTGATCCACC GCGATTCTCC TAAATCGCCA TTCTATAACC CGGGGGAAAC
CCCTTCCCAA CGTATGAGAA AGCTATCCA CCGATCCTTT AACCGTGCTT CCCATTTCAG TAATCTTTTT
GAAAGGATG CATCACTTAA CGCACCACAA ACTGATATCA CCAAATATTT CGGTATATAT CTTATGAACG
TATCCCTTGG GAGTTGGGAC ACCTCCCGTC CCAATCATGG CGGCCGCTGA CACCGGAAGT GATCTCATCT
GGACGCAGTG CAAACCATGC GATGATTGTT ACACTCAAGT TGATCCTCTC TTTGACCCTA AAGGTCTTC
CACATACAAA GACGTTTCTT GCCCCTCAAG CCAATGTAGG GCTCTAAAAG ATGATGCTTC TTGTTCCAAA
AAGACAACA CTTGCTCTTA CTCAATGAAT TACGGGGATA ACTCATACTC ATGATGGGTAAT GTCGCTGTGG
ATACCTTAAC GCTCGGCTCC ACCGATAACC GTCCGGTGCA GGTTAAGAAT ATTATCATCG GTTGTGGTCA
CGAAAACGCT GTAACATTA GAAACAAGAG CTCTGGAATC GTTGGACTTG GTGGTGGTGC GGTTTCGCTC
GTTAAACAAC TCGGAGACTC CATCGAAGGT AATTCTCAT ACTGCTTGGT ACCTGAAAAT GATCAAACGA
GCAAGATTAG TTTCGGAACC AATGCCGGTTG TGTCGGGACC GGGAACTGTC TCAACTCCTT TGGTCGTGAA
GTCTCCAGAG ACCTTCTATT TTCTAACCCT AAAATCTATT ACCGTGGGAA GCAAGAATAT GCCAACCCCA
GGCTCTGATA TCAAGGGAAA CATGGTCATC GATTCGGGCA CAACTCTAAC TCTGTTACCT GGGAAATATT
ATTCCAGAT TGAGAGTGCT GTTGGCTGCTT CCGCAGATCT AATCGATGC GAAGATGAAA GAATCGGTTC
GAGTCTTTGA TACAATGCAA CCGCAGATCT TCATTTTTT AAGTCTCCAG GTCATTACTA TGCATTTCGA TGGAGCAGAT
GTGAAGCTTG ATTCCTATAA ATGCCTATGG ATGATTGGT ATGATTTGGT TGCTTTGCC TTTGGCTTGA
ACTTGATTAC GAGGGATGGG ATATACGGGA ATGTGCGCA GAAGAACTTT CTTGTTGGAT ACGACACTGT
TCCAAATCG TGTCATTTA AAAACAGA ATATACGGGA TGTGCAAAG ATGTAGATGG TTCAGCTTAG CATGTGGCTA
ATTCCTTTTCAAAGTATGTTTTCAGTTTATCATTATGGCTGATTGATTTTAGCCTTAAAATAGTTATTTGAATTC
```

FIG. 3C

SEQUENCE LISTING

```
<160> NUMBER OF SEQ ID NOS: 3

<210> SEQ ID NO 1
<211> LENGTH: 4839
<212> TYPE: DNA
<213> ORGANISM: Arabidopsis thaliana
<220> FEATURE:
<221> NAME/KEY: CDS
<222> LOCATION: (1111)...(2421)

<400> SEQUENCE: 1
ggacattctt ggtctactcc aagaatatca aagatccagt ctcagaagac cagagggcta      60
ttgagacttt tcaacaaagg gtaatatcgg gaaacctcct cggattccat tgcccagcta     120
tctgtcactt catcgaaagg acagtagaaa aggaagatgg cttctacaaa tgccatcatt     180
gcgataaagg aaaggctatc gttcaagatg cctctaccga cagtggtccc aaagatggac     240
ccccacccac gaggaacatc gtggaaaaag aagacgttcc aaccacgtct tcaaagcaag     300
tggattgatg tgatatcaaa gatgcgagag ttattttatt ttaattgtac tatatttata     360
ttgtgatgtt tctcttaaat taaaaattta tgactatata tatgacaata tatatatata     420
tatatatata tatatacatt attgagatag ataatgaata cattagttta tcattaaatt     480
taataggtac tgatcttcaa attattttca aacgattctc tgtcaatttc ttgatatttt     540
taaactaaaa tccatttttt aaaaaataga ctgatttaac aaacattaaa agttaattgt     600
ttctgtacat gccacggatc gaaatgagt cagtaaatga atatttttta cctaaagtca     660
cacattgtat atacctaagt aaatgataca gaccaaaatt agaagatcaa gaatccttat     720
attacgaaaa tatccggtta cattcgttga atactttaat gaagaatcta ggatataatt     780
aaagaagaag aaaatatgta agcatttaga aataaaataa cttggagata taagcaaacc     840
ataaacacgt ccatatgaat gaatggtaca ctcctcgtaa ataaataaat atatgcatca     900
aaatgagaaa atcttcactt ttatttattc ttaatacgtc agattctctg aacacaaaat     960
gatataattt gtagataact tactcaaaac gtaagaactc actatctatt atcatttatt    1020
aaccaccatc tcattaatct tataaatatg tactcattag attgtcaaaa gtaaaacctc    1080
acaatacact ttaaactaca aatcaaaaca atg gcc tct cta ttc tct tca gtt    1134
                                 Met Ala Ser Leu Phe Ser Ser Val
                                  1               5
```

-continued

```
ctc ttg tct ctt tgt tta ctc tct tca ctt ttt ctc tca aat gca aac      1182
Leu Leu Ser Leu Cys Leu Leu Ser Ser Leu Phe Leu Ser Asn Ala Asn
    10              15                  20 gct aag cca aaa cta ggc ttc acc gcg gat cta atc cac cgt gat tct      1230
Ala Lys Pro Lys Leu Gly Phe Thr Ala Asp Leu Ile His Arg Asp Ser
25              30                  35                  40 cct aaa tcg ccg ttc tat aac ccg atg gaa acc tct tcc cag cgt cta      1278
Pro Lys Ser Pro Phe Tyr Asn Pro Met Glu Thr Ser Ser Gln Arg Leu
                45                  50                  55 cga aac gcg atc cac cga tcc gtt aac cgt gtt ttc cat ttc act gaa      1326
Arg Asn Ala Ile His Arg Ser Val Asn Arg Val Phe His Phe Thr Glu
            60                  65                  70 aag gat aac aca cca caa cca cag att gac ctc acc tca aat agc ggt      1374
Lys Asp Asn Thr Pro Gln Pro Gln Ile Asp Leu Thr Ser Asn Ser Gly
        75                  80                  85 gaa tat ctc atg aac gta tcc att gga aca cct cct ttc ccg atc atg      1422
Glu Tyr Leu Met Asn Val Ser Ile Gly Thr Pro Pro Phe Pro Ile Met
    90                  95                  100 gcc atc gcc gac acc gga agt gat ctc ctc tgg acg cag tgc gca cca      1470
Ala Ile Ala Asp Thr Gly Ser Asp Leu Leu Trp Thr Gln Cys Ala Pro
105                 110                 115                 120 tgc gat gat tgt tac act caa gtt gat cct ctc ttt gac cct aaa acg      1518
Cys Asp Asp Cys Tyr Thr Gln Val Asp Pro Leu Phe Asp Pro Lys Thr
                125                 130                 135 tct tcc aca tac aaa gac gtt tct tgc tcc tca agt caa tgt act gcc      1566
Ser Ser Thr Tyr Lys Asp Val Ser Cys Ser Ser Ser Gln Cys Thr Ala
            140                 145                 150 cta gaa aat caa gcc tct tgt tcc aca aat gac aac act tgt tct tac      1614
Leu Glu Asn Gln Ala Ser Cys Ser Thr Asn Asp Asn Thr Cys Ser Tyr
        155                 160                 165 tca ttg tct tac ggg gat aac tca tac aca aag ggt aac atc gcc gtg      1662
Ser Leu Ser Tyr Gly Asp Asn Ser Tyr Thr Lys Gly Asn Ile Ala Val
    170                 175                 180 gat acc tta acg ctc ggc tcc agc gat acc cgc cct atg cag ctt aag      1710
Asp Thr Leu Thr Leu Gly Ser Ser Asp Thr Arg Pro Met Gln Leu Lys
185                 190                 195                 200 aat att att atc ggt tgt ggt cac aac aac gct gga acg ttt aac aag      1758
Asn Ile Ile Ile Gly Cys Gly His Asn Asn Ala Gly Thr Phe Asn Lys
                205                 210                 215 aaa ggc tct gga atc gtc gga cta ggt ggt ggt ccg gtt tcg ctt atc      1806
Lys Gly Ser Gly Ile Val Gly Leu Gly Gly Gly Pro Val Ser Leu Ile
            220                 225                 230 aag caa ctt ggc gac tcc atc gac ggt aaa ttc tca tac tgc ttg gtt      1854
Lys Gln Leu Gly Asp Ser Ile Asp Gly Lys Phe Ser Tyr Cys Leu Val
        235                 240                 245 cct cta act tcc aaa aag gat caa acg agt aaa atc aac ttc gga acc      1902
Pro Leu Thr Ser Lys Lys Asp Gln Thr Ser Lys Ile Asn Phe Gly Thr
    250                 255                 260 aat gcc atc gtg tcg gga tca gga gtt gtc tca act cct ctg atc gca      1950
Asn Ala Ile Val Ser Gly Ser Gly Val Val Ser Thr Pro Leu Ile Ala
265                 270                 275                 280 aag gcg tct caa gag acc ttc tat tac cta acc cta aaa tcc att agc      1998
Lys Ala Ser Gln Glu Thr Phe Tyr Tyr Leu Thr Leu Lys Ser Ile Ser
                285                 290                 295 gtg gga agc aag caa atc caa tac tca ggc tca gat tct gaa agc agc      2046
Val Gly Ser Lys Gln Ile Gln Tyr Ser Gly Ser Asp Ser Glu Ser Ser
            300                 305                 310 gag gga aac atc atc atc gat tca ggc aca act tta acg tta tta ccg      2094
Glu Gly Asn Ile Ile Ile Asp Ser Gly Thr Thr Leu Thr Leu Leu Pro
```

-continued

| | 315 | | | | | 320 | | | | | 325 | | | | |
|---|---|---|---|---|---|---|---|---|---|---|---|---|---|---|---|
| act | gaa | ttt | tac | tcc | gag | ctc | gag | gat | gcg | gtt | gca | tcc | tct | atc | gat | 2142 |
| Thr | Glu | Phe | Tyr | Ser | Glu | Leu | Glu | Asp | Ala | Val | Ala | Ser | Ser | Ile | Asp | |
| | 330 | | | | | 335 | | | | | 340 | | | | | |
| gct | gag | aag | aag | caa | gat | cca | caa | agc | ggt | ttg | agt | cta | tgt | tac | agt | 2190 |
| Ala | Glu | Lys | Lys | Gln | Asp | Pro | Gln | Ser | Gly | Leu | Ser | Leu | Cys | Tyr | Ser | |
| 345 | | | | | 350 | | | | | 355 | | | | | 360 | |
| gca | acc | gga | gat | cta | aaa | gtt | cca | gtc | att | act | atg | cat | ttt | gat | gga | 2238 |
| Ala | Thr | Gly | Asp | Leu | Lys | Val | Pro | Val | Ile | Thr | Met | His | Phe | Asp | Gly | |
| | | | | 365 | | | | | 370 | | | | | 375 | | |
| gcc | gat | gtg | aag | ctt | gac | tcc | tcc | aat | gcc | ttt | gta | caa | gtc | tcg | gag | 2286 |
| Ala | Asp | Val | Lys | Leu | Asp | Ser | Ser | Asn | Ala | Phe | Val | Gln | Val | Ser | Glu | |
| | | | 380 | | | | | 385 | | | | | 390 | | | |
| gat | ttg | gtt | tgc | ttt | gcc | ttc | cgc | gga | agc | ccg | agt | ttc | tcc | ata | tac | 2334 |
| Asp | Leu | Val | Cys | Phe | Ala | Phe | Arg | Gly | Ser | Pro | Ser | Phe | Ser | Ile | Tyr | |
| | | 395 | | | | | 400 | | | | | 405 | | | | |
| ggt | aat | gtg | gcg | cag | atg | aac | ttt | ctt | gtt | gga | tac | gac | act | gtt | tcc | 2382 |
| Gly | Asn | Val | Ala | Gln | Met | Asn | Phe | Leu | Val | Gly | Tyr | Asp | Thr | Val | Ser | |
| | 410 | | | | | 415 | | | | | 420 | | | | | |
| aaa | acg | gtg | tca | ttt | aag | cca | aca | gat | tgt | gca | aag | atg | tagttgtttc | | | 2431 |
| Lys | Thr | Val | Ser | Phe | Lys | Pro | Thr | Asp | Cys | Ala | Lys | Met | | | | |
| 425 | | | | 430 | | | | | 435 | | | | | | | | atctcaacat gttttcaaa attgtgtttt caattacaat aatggctgat ttagtttcag    2491 ccttagttct tttgaatttt tctaattcac atgtagtagt ctatctttc aagggagagt    2551 taaattctcg accttttgtt cttttggtga tgctttgtat ttccttgaat tttcaatcac    2611 aattaaaatc atgaaaacct tatctccggt aactattttc ttgtccatct ctatactctg    2671 ttttagttta taatcatctc tatgatgtaa accaaatatg acaagacaat tctataattt    2731 tgttcaaaat ttagtttttt ttttcatttt actaataaaa tctagaaata ctactttgt    2791 gtctattata ttattgtgat gaaatactta taagaaacag atgaatgtga ttctaattca    2851 atattgcttt taaggaatta tattggtcct actattctat tttgatgtgt tctatatttt    2911 actatattca atgggattat ggattataga aatattttga aaatattata ctattattta    2971 taaataattc aattagtttt tcttcttaag tttcttataa aaataaata tatcttataa    3031 gaaataaata tattttatat ttcataaaaa tcatacattg tacatatcta ggtggatgat    3091 acatggccta aattagatca tgaatcataa aaatccagct gtagataaac ataacaagga    3151 tgaatggtac aatcctggtc aaaaaaaata aaaggaaaag ttatatgcat taaaatgaga    3211 aaatcttcgc ttttattgtt tcttattat cagattctct aaatgtaaat gacacaattt    3271 gtagataatt tactaaaaat gtaagaatct catcatgtac taccatttat gaatccttat    3331 ccaattgacc ttataaatat tactcatcag attgtcaaaa gtaaaaactg accattcagg    3391 caatcactta aactacaatc taagaaaatg gcctctctat tcacttcact tctcttgtct    3451 ctatgtttat tctcttctcc tattttctca aacgcaaacg ccaaaccaaa actaggcttc    3511 accgcggatc tgatccaccg cgattctcct aaatcgccat tctataaccc ggcggaaacc    3571 ccttcccaac gtatgagaaa cgctatccac cgatccttta accgtgcttc ccatttcagt    3631 aatcttttg aaaaggatgc atacttaac gcaccacaaa ctgatatcac caaatatttc    3691 ggtatatatc ttatgaacgt atcccttggg agttgggaca cctcccgtcc caatcatggc    3751 ggccgctgac accggaagtg atctcatctg gacgcagtgc aaaccatgcg atgattgtta    3811 cactcaagtt gatcctctct tgacccctaa agcgtcttcc acatacaaag acgtttcttg    3871 cccctcaagc caatgtaggg ctctaaaaga tgatgcttct tgttccaaaa aagacaacac    3931

-continued

```
ttgctcttac tcaatgaatt acggggataa ctcatactca cggggtaatg tcgctgtgga    3991
taccttaacg ctcggctcca ccgataaccg tccggtgcag gttaagaata ttatcatcgg    4051
ttgtggtcac gaaaacgctg taacatttag aaacaagagc tctggaatcg ttggacttgg    4111
tggtggtgcg gtttcgctcg ttaaacaact cggagactcc atcgaaggta aattctcata    4171
ctgcttggta cctgaaaatg atcaaacgag caagattagt ttcggaacca atgcggttgt    4231
gtcgggaccg ggaactgtct caactccttt ggtcgtgaag tctccagaga ccttctattt    4291
tctaacccta aaatctatta ccgtgggaag caagaatatg ccaaccccag gctctgatat    4351
caagggaaac atggtcatcg attcgggcac aactctaact ctgttacctg ggaaatatta    4411
tttccagatt gagagtgctg ttgcgtcttt aatcgatgca gagaggtcga agatgaaag    4471 aatcggttcg agtctttgat acaatgcaac cgcagatctg aaagtcccag tcattactat    4531
gcatttcgat ggagcagatg tgaagcttga ttcctataat tcattttta aagtctcaga    4591 tgatttggtt tgctttgcct ttggcttgaa cttgattacg agggatggga tatacgggaa    4651
tgtggcgcag aagaactttc ttgttggata cgacactgtt tccaaatcgt tgtcatttaa    4711
aaaaacagat tgtgcaaaga tgtagatggt tcagcttagc atgtggctaa tttccttttt    4771
tcaaaagtat gttttcagtt atcattatgg ctgatttgat tttagcctta aaatagttat    4831
ttgaattc                                                             4839
```

```
<210> SEQ ID NO 2
<211> LENGTH: 437
<212> TYPE: PRT
<213> ORGANISM: Arabidopsis thaliana

<400> SEQUENCE: 2

Met Ala Ser Leu Phe Ser Ser Val Leu Leu Ser Leu Cys Leu Leu Ser
 1               5                  10                  15

Ser Leu Phe Leu Ser Asn Ala Asn Ala Lys Pro Lys Leu Gly Phe Thr
                20                  25                  30

Ala Asp Leu Ile His Arg Asp Ser Pro Lys Ser Pro Phe Tyr Asn Pro
            35                  40                  45

Met Glu Thr Ser Ser Gln Arg Leu Arg Asn Ala Ile His Arg Ser Val
        50                  55                  60

Asn Arg Val Phe His Phe Thr Glu Lys Asp Asn Thr Pro Gln Pro Gln
65                  70                  75                  80

Ile Asp Leu Thr Ser Asn Ser Gly Glu Tyr Leu Met Asn Val Ser Ile
                85                  90                  95

Gly Thr Pro Pro Phe Pro Ile Met Ala Ile Ala Asp Thr Gly Ser Asp
                100                 105                 110

Leu Leu Trp Thr Gln Cys Ala Pro Cys Asp Asp Cys Tyr Thr Gln Val
            115                 120                 125

Asp Pro Leu Phe Asp Pro Lys Thr Ser Thr Tyr Lys Asp Val Ser
        130                 135                 140

Cys Ser Ser Ser Gln Cys Thr Ala Leu Glu Asn Gln Ala Ser Cys Ser
145                 150                 155                 160

Thr Asn Asp Asn Thr Cys Ser Tyr Ser Leu Ser Tyr Gly Asp Asn Ser
                165                 170                 175

Tyr Thr Lys Gly Asn Ile Ala Val Asp Thr Leu Thr Leu Gly Ser Ser
            180                 185                 190

Asp Thr Arg Pro Met Gln Leu Lys Asn Ile Ile Ile Gly Cys Gly His
        195                 200                 205
```

```
Asn Asn Ala Gly Thr Phe Asn Lys Lys Gly Ser Gly Ile Val Gly Leu
    210                 215                 220

Gly Gly Gly Pro Val Ser Leu Ile Lys Gln Leu Gly Asp Ser Ile Asp
225                 230                 235                 240

Gly Lys Phe Ser Tyr Cys Leu Val Pro Leu Thr Ser Lys Lys Asp Gln
                245                 250                 255

Thr Ser Lys Ile Asn Phe Gly Thr Asn Ala Ile Val Ser Gly Ser Gly
                260                 265                 270

Val Val Ser Thr Pro Leu Ile Ala Lys Ala Ser Gln Glu Thr Phe Tyr
            275                 280                 285

Tyr Leu Thr Leu Lys Ser Ile Ser Val Gly Ser Lys Gln Ile Gln Tyr
    290                 295                 300

Ser Gly Ser Asp Ser Glu Ser Ser Glu Gly Asn Ile Ile Ile Asp Ser
305                 310                 315                 320

Gly Thr Thr Leu Thr Leu Leu Pro Thr Glu Phe Tyr Ser Glu Leu Glu
                325                 330                 335

Asp Ala Val Ala Ser Ser Ile Asp Ala Glu Lys Lys Gln Asp Pro Gln
                340                 345                 350

Ser Gly Leu Ser Leu Cys Tyr Ser Ala Thr Gly Asp Leu Lys Val Pro
            355                 360                 365

Val Ile Thr Met His Phe Asp Gly Ala Asp Val Lys Leu Asp Ser Ser
    370                 375                 380

Asn Ala Phe Val Gln Val Ser Glu Asp Leu Val Cys Phe Ala Phe Arg
385                 390                 395                 400

Gly Ser Pro Ser Phe Ser Ile Tyr Gly Asn Val Ala Gln Met Asn Phe
                405                 410                 415

Leu Val Gly Tyr Asp Thr Val Ser Lys Thr Val Ser Phe Lys Pro Thr
                420                 425                 430

Asp Cys Ala Lys Met
            435

<210> SEQ ID NO 3
<211> LENGTH: 14
<212> TYPE: PRT
<213> ORGANISM: Artificial Sequence
<220> FEATURE:
<223> OTHER INFORMATION: synthetic peptide utilized for antibody
      production; segment of SEQ ID NO:2

<400> SEQUENCE: 3

Asp Thr Val Ser Lys Thr Val Ser Phe Lys Pro Thr Asp Cys
1               5                   10
```

CONSTITUTIVE DISEASE RESISTANCE (CDR1) GENE AND METHODS OF USE THEREOF

RELATED APPLICATIONS

This application claims priority under 35 U.S.C. § 119 (e)(1)-to U.S. Provisional Application Ser. No. 60/092,696, filed Jul. 14, 1998, which is incorporated by this reference in its entirety.

FIELD OF THE INVENTION

The present invention relates generally to disease resistance in plants and more specifically to a plant resistance factor, constitutive disease resistance 1 (CDR1), polynucleotides encoding CDR1, and methods of use thereof for producing transgenic plants having increased pathogen resistance.

BACKGROUND OF THE INVENTION

A plant is considered healthy when it can carry out its physiological functions, such as cell division, differentiation, development, photosynthesis, absorption and translocation of water and nutrients from the soil, metabolism, reproduction, and storage of food supplies, without disruption. When plant functions are disturbed by pathogens, the plants become diseased. Disease can be defined as the malfunctioning of plant host cells and tissues caused by continuous irritation by a pathogenic agent. A disease involves abnormal changes in the form, physiology, or behavior of the plant.

Plant pathogens cause disease by weakening the plant by absorbing food from the plant cells, secreting toxins, enzymes, or growth regulating substances that disturb or kill the plant cells, or block the transport of food nutrients or water in the plant. The roots, stems, leaves, flowers, or fruits can be infected. The affected cells and tissues are weakened or destroyed, and cannot perform normal physiological functions, resulting in reduction of plant growth or death, and reducing crop quality or yield. The major causes of plant diseases are bacteria, mycoplasmas, viruses, nematodes, and fungi. Fugal species from a variety of genera affect plants, including Fusarium, Pythium, Phytophthora, Verticillium, Rhizoctonia, Macrophonmina, Thielaviopsis, Sclerotinia, and numerous others. Plant disease caused by fungi include pre- and post-emergence seedling damping-off, hypocotyl rots, root rots, crown rots, vascular wilt, and other symptoms. Nematodes harmful to plants include nematode species form the genera Meloidogyne, Heterodera, Ditylenchus, and Pratylencus. Plant diseases caused by nematodes include root galls, root rot, lesions, "stubby" root, stunting, and other rots and wilts. Some nematodes (e.g., Trichodorus, Lonoidorus, xipenema) can serve as vectors for virus diseases in a number of plants including Prunus, grape, tobacco, and tomato.

Plant pathogenic bacteria cause a variety of plant disease symptoms. About 80 species of bacteria (e.g., *Pseudomonas viridiflava, Xanthomonas campestris pv. asclepiadas, Xyellafastidiosa, Acidovorax albilineans,* and *Acidovorax avenae sspl citrulli*) cause disease in plants, including fruit rot, galls, wilts, blight, and leaf spots. As bacteria multiply quickly, controlling them early in the disease process is critical. Copper and streptomycin compounds are the only chemical compounds currently available for the control of bacterial diseases.

The response of plants to microbial attack involves de novo synthesis of an array of proteins designed to restrict the growth of the pathogen. These proteins include hydroxyproline-rich glycoproteins, proteinase inhibitors, enzymes for the synthesis of phyoalexins, enzymes contributing to the reinforcement of cell walls, and certain hydrolytic enzymes.

Plant defenses can also be activated by elicitors derived from microbial cell walls and culture fluids. In dicotyledonous plants, extensive studies have shown that microbial attack or elicitor treatments induces the transcription of a battery of genes encoding proteins involved in the defense response, as part of a massive switch in the overall pattern of gene expression. In contrast, little is known about the inducible defenses in monocotyledonous plants.

Genetic engineering of plants, which entails the isolation and manipulation of genetic material, e.g., DNA or RNA, and the subsequent introduction of that material into a plant or plant cells, has changed plant breeding and agriculture considerably over recent years. Increased crop food values, higher yields, feed value, reduced production costs, pest resistance, stress tolerance, drought resistance, the production of pharmaceuticals, chemicals and biological molecules as well as other beneficial traits are all potentially achievable through genetic engineering techniques. Genetic engineering techniques supplying the genes involved in pathogen resistance have the potential to substantially affect crop production.

SUMMARY OF THE INVENTION

The present invention is based on the discovery of a constitutive disease resistance (CDR1) factor that confers enhanced disease resistance on plants, including resistance to infection by the pathogens *Pseudomonas syringe pv. tomato* (Pst) or *P. syringe pv. maculicola* (Psm, for example).

In one embodiment, substantially purified CDR1 polypeptide is provided. Isolated polynucleotides encoding CDR1 polypeptide, as exemplified by SEQ ID NO:1, are also provided. Vectors containing CDR1, host cells expressing CDR1, and antibodies bind that bind to CDR1 are further provided.

In another embodiment, the invention provides a method of producing a genetically modified plant characterized as having increased disease resistance as compared to a corresponding wild-type plant. The method includes contacting plant cells with nucleic acid encoding an CDR1 polypeptide, operatively associated with an expression control sequence, to obtain transformed plant cells; producing plants from the transformed plant cells; and selecting a plant exhibiting increased disease resistance. A method for genetically modifying a plant cell such that a plant produced from the cell is characterized as having increased disease resistance as compared with a wild-type plant is also provided. The method includes introducing an isolated polynucleotide encoding a CDR1 polypeptide into a plant cell to obtain a transformed plant cell, and growing the transformed plant cell under conditions which permit expression of CDR1 polynucleotide thereby producing a plant having increased disease resistance.

In a further embodiment, a method is provided for producing a genetically modified plant characterized as having increased disease resistance as compared to the corresponding wild type plant by contacting a susceptible plant with a CDR1 promoterinducing amount of an agent necessary to elevate CDR1 gene expression above CDR1 expression in a plant not contacted with the agent. For example, the agent may be a transcription factor or a chemical agent, such as dexamethasone (DEX).

A method is also provided for producing genetically transformed, disease resistant plants, by introducing into the genome of a plant cell, to obtain a transformed plant cell, a nucleic acid sequence having an expression control sequence operably linked to a polynucleotide encoding a CDR1 polypeptide. The invention also provides plants, plant tissue, and seeds produced by plants produced by the methods of the invention.

In yet another embodiment, a method is provided for identifying novel disease resistance genes by probing a nucleic acid libray with at least a fragment of a polynucleotide encoding CDR1, and selecting those clones that hybridize with the fragment.

BRIEF DESCRIPTION OF THE DRAWINGS

FIG. 1 is a schematic diagram of the activation tagging binary vector pSK15.

FIGS. 3A and 3B are the genomic sequence of CDR1 and the deduced amino acid sequence (SEQ ID NO: 1 and SEQ ID NO:2, respectively).

DESCRIPTION OF THE PREFERRED EMBODIMENTS

Figure 2:
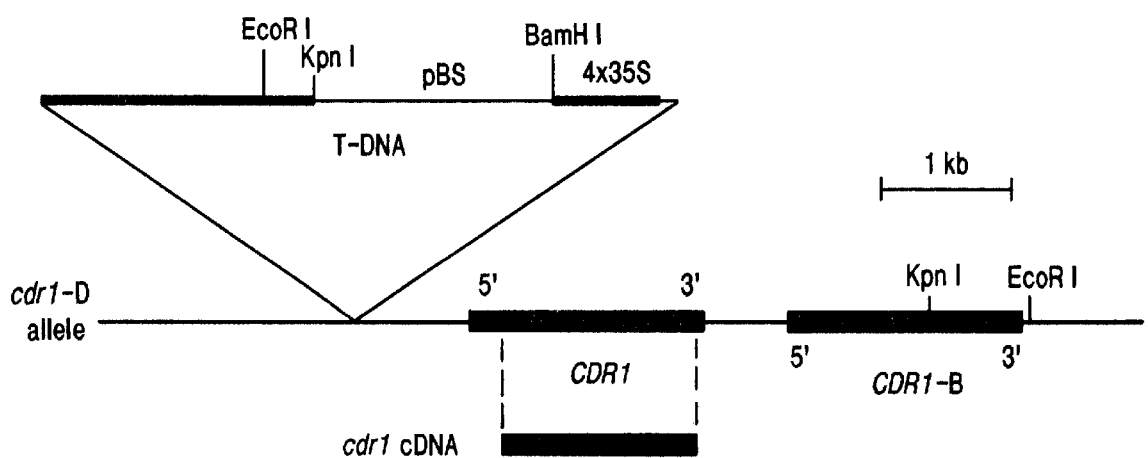
FIG. 2 is a drawing of the organization of pCDR1E and pCDR1C1.

It must be noted that as used herein and in the appended claims, the singular forms "a", "and", and "the" include plural referents unless the context clearly dictates otherwise. Thus, for example, reference to "a cell" includes a plurality of such cells and reference to "the receptor" includes reference to one or more receptors and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference in full for the purpose of describing and disclosing the cell lines, chemokines, and methodologies which are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

This invention provides a constitutive disease resistance (CDR1) polypeptide, polynucleotide and methods of use. CDR1 confers resistance to plant pathogens and is therefore useful in the production of genetically modified pest-resistant plants.

Polynucleotides Polyepeptides, Vector, and Host Cells

The invention provides substantially purified CDR1 polypeptide. Preferably, CDR1 has an amino acid sequence as set forth in SEQ ID NO:2, and conservative variants thereof (see FIG. 3). The term "substantially purified" as used herein refers to a polypeptide which is substantially free of other proteins, lipids, carbohydrates or other materials with which it is naturally associated. One skilled in the art can purify CDR1 using standard techniques for protein purification. The substantially pure polypeptide will yield a single major band on a non-reducing polyacrylamide gel. The purity of the CDR1 polypeptide can be determined by amino-terminal amino acid sequence analysis.

The invention includes functional CDR1 polypeptide as well as functional fragments thereof As used herein, the tenn "functional polypeptide" refers to a polypeptide which possesses biological function or activity which is identified through a defined functional assay and which is associated with a particular biologic, morphologic, or phenotypic alteration in the cell. The term functional fragments of CDR1 polypeptide, refers to all fragments of CDR1 that retain a CDR1 activity. Biologically functional fragments, for example, can vary in size from a polypeptide fragment as small as an epitope capable of binding an antibody molecule to a large polypeptide capable of participating in the characteristic induction or programming of phenotypic changes within a cell. A specific, nonlimiting example of a functional fragment of CDR1 is a polypeptide encoding a domain able to increase the level of PR-1, PR-2 or RbohA transcription. Alternatively, a functional fragment can confer disease resistance to a particular pathogen, or can bind DNA and activate transcription or a CDR1-regulated gene.

Minor modifications of the CDR1 primary amino acid sequences may result in proteins which have substantially equivalent activity as compared to the unmodified counterpart polypeptide described herein. Such modifications may be deliberate, as by site-directed mutagenesis, or may be spontaneous. All of the polypeptides produced by these modifications are included herein as long as a biological activity of CDR1 still exists. Further, deletion of one or more amino acids can also result in a modification of the structure of the resultant molecule without significantly altering its activity. Deletion can lead to the development of a smaller active molecule which could have broader utility. For example, it may be possible to remove amino or carboxy terminal amino acids required for CDR1 activity. Dominant negative forms of CDR1 are also included herein.

CDR1 polypeptide includes amino acid sequences substantially the same as the sequence set forth in SEQ ID NO:2. The term substantially the same refers to amino acid sequences that retain the activity of CDR1 as described herein, e.g., confer resistance to plant pathogens. The CDR1 polypeptides of the invention include conservative variations of the polypeptide sequence. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginie for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

In yet another embodiment, the invention provides a substantially purified polypeptide characterized as having a molecular weight of about 4.5 kDa by PAGE; being induced by CDR1 polypeptide; and having a biological activity that induces disease resistance in plants. Example 13 provides experimental evidence that CDR1 expression results in specific induction of a 4.5 kDa protein. While not wanting to be bound by a particular theory, it is believed that this protein may be responsible for providing disease resistance in plants. Thus, once isolated, the 4.5 kDa protein may be independently utilized to provide disease resistance in plants, and anti-4.5 kDa antibodies may be usefull in increasing susceptibility to disease in plants.

The invention provides polynucleotides encoding the CDR1 protein. These polynucleotides include DNA, cDNA and RNA sequences which encode CDR1. It is understood that all polynucleotides encoding CDR1 are also included herein, as long as they encode a polypeptide with a CDR1 activity or fragments thereof Such polynucleotides include naturally occurring, synthetic, and intentionally manipulated polynucleotides. For example, CDR1 polynucleotide may be subjected to site-directed mutagenesis. The polynucleotide sequence for CDR1 also includes antisense sequences, and sequences encoding dominant negative forms of CDR1. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of CDR1 polypeptide encoded by the nucleotide sequence is functionally unchanged.

Specifically disclosed herein is a nucleic acid sequence encoding CDR1 polypeptide (FIG. 3). An exemplary CDR1 nucleotide sequence is set forth in SEQ ID NO: 1. The term polynucleotide or nucleic acid sequence refers to a polymeric form of nucleotides at least 10 bases in length. By isolated polynucleotide is meant a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g. a cDNA) independent of other sequences. The nucleotides of the invention can be ribonucleotides, deoxyribonucleotides, or modified forms of either nucleotide. The term includes single and double forms of DNA.

A polynucleotide encoding CDR1 includes SEQ ID NO:1, polynucleotides encoding dominant negative forms of CDR1, and nucleic acid sequences complementary to SEQ ID NO:1. A complementary sequence may include an antisense nucleotide. When the sequence is RNA, the deoxynucleotides A, G, C, and T of SEQ ID NO:1 are replaced by ribonucleotides A, G, C, and U, respectively. Also included in the invention are fragments of the above-described nucleic acid sequences and are at least 15 bases in length, which is sufficient to permit the fragment to selectively hybridize to DNA that encodes the protein of SEQ ID NO:2 under physiological conditions or a close family member of CDR1. Degenrate variants of SEQ ID NO:1, SEQ ID NO:1 where T can also be a U, and fragments of that are at least 15 bases in length that will hybrize to DNA or RNA which encodes CDR1 are also included. The term selectively hybridize refers to hybridization under moderately or highly stringent conditions which excludes non-related nucleotide sequences.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g. RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42/C (moderate stringency conditions); and 0.1×SSC at about 68/C (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

DNA sequences encoding CDR1 can be expressed in vitro by DNA transfer into a suitable host cell. "Host cells" are cells in which a vector can be propagated and its DNA expressed. The cell may be plant cells, or prokaryotic or eukaryotic cells. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the CDR1 polynucleotide sequences may be inserted into an expression vector. The term "expression vector" refers to a plasmid, virus or other vehicle known in the art that has been manipulated by insertion or incorporation of the CDR1 genetic sequences. Polynucleotide sequence which encode CDR1 can be operatively linked to expression control sequences. Operatively linked refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. As used herein, the term expression control sequences refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, as start codon (i.e., ATG) in front of a protein-encoding gene, splicing signal for introns, maintenance of the correct reading frame of that gene to permit proper translation of mRNA, and stop codons. The term control sequences is intended to included, at a minimum, components whose presence can influence expression, and can also include additional components whose presence is advantageous, for example, leader sequences and fusion partner sequences. Expression control sequences can include a promoter.

By promoter is meant minimal sequence sufficient to direct transcription. Also included in the invention are those promoter elements which are sufficient to render promoter-dependent gene expression controllable for cell-type specific, tissue-specific, or inducible by external signals or agents; such elements may be located in the 5' or 3' regions of the gene.

Optionally, a selectable marker may be associated with the CDR1 polynucleotide. As used herein, the term "marker"

refers to a gene encoding a trait or a phenotype which permits the selection of, or screening for, a cell containing the marker. Preferably, the marker gene is an antibiotic resistance gene whereby the appropriate antibiotic can be used to select for transformed cells from among cells that are not transformed. Examples of suitable selectable markers for use in plants include adenosine deaminase, dihydrofolate reductase, hygromycin-B-phosphotransferase, thymidine kinase, xanthine-guanine phospho-ribosyltransferase and amino-glycoside 3'-O-phosphotransferase II (kanamycin, neomycin and G418 resistance). Other suitable markers will be known to those of skill in the art.

A variety of host-expression vector systems may be utilized to express the CDR1 coding sequence. These include but are not limited to microorganisms such as bacteria transformed with recombinant bacteriophage nucleic acid, plasmid nucleic acid or cosmid nucleic acid expression vectors containing the CDR1 coding sequence; yeast transformed with recombinant yeast expression vectors containing the CDR1 coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the CDR1 coding sequence; insect cell systems infected with recombinant virus expression vectors (e.g., baculovirus) containing the CDR1 coding sequence; or animal cell systems infected with recombinant virus expression vectors (e.g., retroviruses, adenovirus, vaccinia virus) containing the CDR1 coding sequence, or transformed animal cell systems engineered for stable expression.

CDR1 Antbodies

The CDR1 polypeptides of the invention can be used to produce antibodies which are immunoreactive or bind to epitopes of the CDR1 polypeptides. Antibodies which consist essentially of pooled monoclonal antibodies with different epitopic specificities, as well as distinct monoclonal antibody preparations are provided.

The preparation of polyclonal antibodies is well-known to those skilled in the art. See, for example, Green et al., Production of Polyclonal Antisera, in: *Immunochemical Protocols*, pages 1–5, Manson, ed., Humana Press, 1992; and Coligan et al., Production of Polyclonal Antisera in Rabbits, Rats, Mice and Hamsters, in: *Current Protocols in Immunology*, section 2.4.1, 1992; which are hereby incorporated by reference.

The preparation of monoclonal antibodies likewise is conventional. See, for example, Kohler and Milstein, *Nature* 256:495, 1975; Coligan et al., sections 2.5.1–2.6.7, supra; and Harlow et al., in: *Antibodies: a Laboratory Manual*, page 726, Cold Spring Harbor Pub., 1988; which are hereby incorporated by reference. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan et al., sections 2.7.1–2.7.12 and sections 2.9.1–2.9.3, supra; Barnes et al., Purification of Immunoglobulin G (IgG), in: *Methods in Molecular Biology*, Vol. 10, pages 79–104, Humana Press, 1992.

Methods of in vitro and in vivo multiplication of monoclonal antibodies are well known to those skilled in the art. Multiplication in vitro may be carried out in suitable culture media such as Dulbecco's Modified Eagle Medium or RPMI 1640 medium, optionally supplemented by a mammalian serum such as fetal calf serum or trace elements and growth-sustaining supplements such as normal mouse peritoneal exudate cells, spleen cells, thymocytes or bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, e.g. syngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

The term "antibody" as used in this invention includes intact molecules as well as fragments thereof, such as Fab, $F(ab')_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) $(Fab')_2$, the fragment of the antibody that can be obtained by treating whole antibody with the enzyme pepsin without subsequent reduction; $F(ab')_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See, for example, Harlow and Lane, *Antibodies: A Laboratory Manual*, Cold Spring Harbor Laboratory, New York, 1988, incorporated herein by reference). As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibody fragments of the present invention can be prepared by proteolytic hydrolysis of the antibody or by expression in E. coli of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. No. 4,036,945 and U.S. Pat. No. 4,331,647, and references contained therein. These patents are hereby incorporated in their entireties by reference. See also Nisonhoffet al., *Arch. Biochem. Biophys.* 89:230, 1960; Porter, *Biochem. J.* 73:119, 1959; Edelman et al., *Methods in Enzymology*, Vol. 1, page 422, Academic Press, 1967; and Coligan et al. at sections 2.8.1–2.8.10 and 2.10.1–2.10.4, supra.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association may be noncovalent, as described in Inbar et al., *Proc. Nat'l Acad. Sci. USA* 69:2659, 1972. Alternatively, the variable chains can be linked by an intermolecular disulfide bond or cross-linked by chemicals such as glutaraldehyde. See, e.g., Sandhu, supra. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by Whitlow et al., *Methods: a Companion to Methods in Enzymology*, Vol. 2, page 97, 1991; Bird et al., *Science* 242:423–426, 1988; Ladner et al., U.S. Pat. No. 4,946,778; Pack et al., *Bio/Technology* 11:1271–77, 1993; and Sandhu, supra.

Another form of an antibody fragment is a peptide coding for a single complementarity-determining region (CDR). CDR peptides ("mnimmal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., *Methods: a Companion to Methods in Enzymology*, Vol. 2, page 106, 1991.

Antibodies which bind to the CDR1 polypeptide of the invention can be prepared using an intact polypeptide or fragments containing small peptides of interest as the immunizing antigen. In an illustrative example, a peptide as described in Example 14(6), DTVSKTVSFKPTDC, was utilized for antibody production. The polypeptide or a peptide used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan et al., Unit 9, *Current Protocols in Immunology*, Wiley Interscience, 1991, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the image of the epitope bound by the first monoclonal antibody.

Genetically Modified Plants and Methods of Making

In another embodiment, the invention provides a method for producing a genetically modified plant characterized as having increased disease resistance as compared to a plant which has not been genetically modified (e.g., a wild-type plant). The term disease resistance or pathogen resistance refers to the ability to maintain a desirable phenotype upon exposure to infection, relative to a nontransgenic plant. The level of resistance can be determined by comparing the physical characteristics of the invention plant to nontransgenic plants that either have or have not been exposed to infection. Exemplary physical characteristics to observe include an increase in population of plants that have the ability to survive pathogen challenge, delayed lesion development, reduced lesion size, and the like. The term "disease" refers to a pathogen challenge caused any agent known to cause symptoms of infection in plants, including, but not limited to bacteria, nematodes, viruses, mycoplasmas, and fungi. In a preferred embodiment, the pathogen is a bacterial pathogen, including, but not limited to, Pseudomonas. Exemplary organisms include *Pseudomonas syringe pv. tomato* (Pst) and *Pseudomonas syringe pv. maculicola* (Psm). The term "increased resistance to pathogens" or "increased resistance to disease" refers to a level of resistance that an invention transgenic plant has to plant pathogens above a defined reference level such as the level of resistance displayed by nontransgenic plants of the same species. Thus, the increased resistance is measured relative to previously existing plants of the same species. In one embodiment, the resistance is substantially increased above the defined reference level greater than or equal to a 20% increase, preferably greater than or equal to a 50% increase, more preferably greater than or equal to a 75% increase, with the most preferred being a 95% increase and above. The phase "nontransgenic plant of the same species" means a plant of the same species that does not contain any heterologous transgenes, or does not contain any transgenes containing a sequence derived from CDR1. The term "heterologous nucleic acid sequence" as used herein refers to a nucleic acid foreign to the recipient plant host or, native to the host if the native nucleic acid is substantially modified from its original form. The levels of pathogen resistance can be determined using methods well known to one of skill in the art. These methods include bacterial resistance assays and fungal infection assays described in U.S. Pat. No. 5,530,187, herein incorporated by reference.

The method of the invention comprises the steps of introducing at least one—nucleic acid sequence encoding CDR1 into a plant cell to obtain a transformed plant cell, wherein the nucleic acid sequence is operably associated with a promoter; producing a plant from the transformed plant cell under conditions which allow expression of CDR1 polynucleotide to produce CDR1 polypeptide; and thereafter selecting a plant exhibiting increased pathogen resistance. The plant may be either a magnitude or a dicot. Examples of monocotyledonous plants include, but are not limited to, asparagus, field and sweet corn, barley, wheat, rice (e.g., Japonica or Indica), sorghum, onion, pearl millet, rye and oats. Examples of dicotyledonous plants include, but are not limited to tomato, tobacco, cotton, rapist, field beans, soybeans, potatoes, grapes, strawberries, peppers, lettuce, peas, alfalfa, clover, Cole crops or *Brassica oleracea* (e.g., cabbage, broccoli, cauliflower, brussel sprouts), radish, carrot, beets, eggplant, spinach, cucumber, squash, melons, cantaloupe, sunflowers and various ornamentals. Woody species include poplar, pine, sequoia, cedar, oak, and the like.

The term "genetic modification" as used herein refers to the introduction of one or more heterologous nucleic acid sequences into one or more plant cells, to provide sexually competent, viable plants. The term "genetically modified" as used herein refers to a plant which has been generated through the aforementioned process. Genetically modified plants of the invention are capable of self-pollinating or cross-pollinating with other plants of the same species so that the foreign gene, carried in the germ line, can be inserted into or bred into agriculturally useful plant varieties. The term "plant cell" as used herein refers to protoplasts, gamete producing cells, and cells which regenerate into whole plants. Accordingly, a seed comprising multiple plant cells capable of regenerating into a whole plant, is included in the definition of "plant cell.

As used herein, the term "plant" refers to either a whole plant, a plant part, a plant cell, or a group of plant cells, such as plant tissue, for example. Plantlets are also included within the meaning of "plant. Plants included in the invention are any plants amenable to transformation techniques, including angiosperms, gymnosperms, monocotyledons and dicotyledons.

The term "heterologous nucleic acid sequence" has been defined above. Any nucleic acid sequence of interest may be used with the subject invention. For example, the term includes a nucleic acid originating in the host species, where such sequence is operably linked to a promoter that differs from the natural or wild-type promoter. In the broad method of the invention, at least one nucleic acid sequence encoding CDR1 polypeptide is associated with a suitable promoter. It may be desirable to introduce more than one copy of CDR1 polynucleotide into a plant for enhanced CDR1 expression. For example, multiple copies of the gene would have the effect of increasing production of CDR1 polypeptide in the plant allowing for greater disease resistance.

Genetically modified plants of the present invention are produced by introducing into a plant cell, a vector including at least one nucleic acid sequence encoding CDR1. To be effective once introduced into plant cells, the CDR1 nucleic acid sequence must be operably associated with a promoter which is effective in the plant cells to cause transcription of CDR1. Additionally, a polyadenylation sequence or transcription control sequence, also recognized in plant cells may also be employed. It is preferred that the vector harboring the nucleic acid sequence to be inserted also contain one or more selectable marker genes so that the transformed cells can be selected from non transformed cells in culture, as described herein.

The expression of CDR1 polynucleotides in the present invention may be driven by a number of promoters. The endogenous, or native promoter of an CDR1 may be utilized for transcriptional regulation of the gene, or a heterologous promoter that is a foreign regulatory sequence may be utilized. For plant expression vectors, suitable viral promoters include the 35S RNA and 19S RNA promoters of CaMV (Brisson et al., *Nature* 310:511, 1984; Odell et al., *Nature* 313:810, 1985); the full-length transcript promoter from Figwort Mosaic Virus (FMV) (Gowda et al., *J. Cell Biochem.* 13D:301, 1989) and the coat protein promoter to TMV (Takamatsu et al., *EMBO J.* 6:307, 1987). Alternatively, plant promoters such as the light-inducible promoter from the small subunit of ribulose bis-phosphate carboxylase (ssRUBISCO) (Coruzzi et al., *EMBO J.* 3:1671, 1984; Broglie et al., *Science* 224:838, 1984); mannopine synthase promoter (Velten et al., *EMBO J.* 3:2723, 1984) nopaline synthase (NOS) and octopine synthase (OCS) promoters (carried on tumor-inducing plasmids of Agrobacterium tumefaciens) or heat shock promoters, e.g., soybean hsp17.5-E or hsp17.3-B (Gurley et al., *Mol. Cell. Biol.* 6:559, 1986; Severin et al., *Plant Mol. Biol.*, 15:827, 1990) may be used.

Promoters useful in the invention include both natural constitutive and inducible promoters as well as engineered promoters. The CaMV promoters are examples of constitutive promoters. To be most useful, an inducible promoter should 1) provide low expression in the absence of the inducer; 2) provide high expression in the presence of the inducer; 3) use an induction scheme that does not interfere with the normal physiology of the plant; and 4) have no effect on the expression of other genes. Examples of inducible promoters useful in plants include those induced by chemical means, such as the yeast metallothionein promoter which is activated by copper ions (Mett et al., *Proc. Natl. Acad. Sci. U.S.A.* 9:4567, 1993); In2-1 and In2-2 regulator sequences which are activated by substituted benzenesulfonamides, e.g., herbicide safeners (Hershey et al., *Plant Mol. Biol.*, 17:679, 1991); and the GRE regulatory sequences which are induced by glucocorticoids (Schena et al., *Proc. Natl. Acad. Sci U.S.A.* 88:10421, 1991) (See Example 10). Other promoters, both constitutive and inducible will be known to those of skill in the art.

The particular promoter selected should be capable of causing sufficient expression to result in the production of an effective amount of structural gene product, e.g., CDR1 polypeptide, to cause increased disease resistance, ultimately resulting in increased plant yield. The promoters used in the vector constructs of the present invention may be modified, if desired, to affect their control characteristics.

Tissue specific promoters may also be utilized in the present invention. An example of a tissue specific promoter is the promoter active in shoot meristems (Atanassova et al., *Plant J.* 2:291, 1992). Other tissue specific promoters useful in transgenic plants, such as the cdc2a promoter and cycO7 promoter, will be known to those of skill in the art. (See, for example, Ito et al., *Plant Mol. Bio.*, 24:863, 1994; Martinez et al., *Proc. Natl. Acad. Sci. USA* 89:7360, 1992; Medford et al., *Plant Cell* 3:359, 1991; Terada et al., *Plant Journal*, 2:241, 1993; Wissenbach et al., *Plant Journal* 4:411, 1993). There are promoters known which limit expression to particular plant parts or in response to particular stimuli (e.g., the patatin promoters or the promoters for the large or small subunits of ADP glucose pyrophosphorylase). These promoters which limit expression, such as those that direct expression to roots, could be operably associated with CDR1 to direct expression primarily in the tuber. One skilled in the art will know of many such plant part-specific promoters which would be useful in the present invention.

Promoters used in the nucleic acid constructs of the present invention may be modified, if desired, to affect their control characteristics. For example, the CaMV 35S promoter may be ligated to the portion of the ssRUBISCO gene that represses the expression of ssRUBISCO in the absence of light, to create a promoter which is active in leaves but not in roots. The resulting chimeric promoter may be used as described herein. For purposes of this description, the phrase "CaMV 35S" promoter thus includes variations of CaMV 35S promoter, e.g., promoters derived by means of ligation with operator regions, random or controlled mutagenesis, etc. Furthermore, the promoters may be altered to contain multiple "enhancer sequences" to assist in elevating gene expression.

Alternatively, the promoters utilized may be selected to confer specific expression of CDR1 in response to disease such as fungal infection. The infection of plants by fungal pathogens activate defense-related or pathogenesis-related (PR) genes which encode (1) enzymes involved in phenylpropanoid metabolism such as phenylalanine ammonia lyase, chalcone synthase, 4-coumarate coA ligase and coumaric acid 4-hydroxylase, (2) proteins that modify plant cell walls such as hydroxyproline-rich glycoproteins, glycine-rich proteins, and peroxidases, (3) enzymes, such as chitinases and glucanases, that degrade the fungal cell wall, (4) thaumatin-like proteins, or (5) proteins of as yet unknown function. The defense-related or PR genes have been isolated and characterized from a number of plant species. The promoters of these genes may be used to obtain expression of CDR1 in transgenic plants when such plants are challenged with a pathogen, particularly a fungal pathogen such as Pi. The particular promoter selected should be capable of causing sufficient expression of CDR1 to result in the production of an effective amount of polypeptide.

Optionally, a selectable marker may be associated with the nucleic acid sequence to be inserted. The term "marker" has been defined above. Preferably, the marker gene is an antibiotic resistance gene whereby the appropriate antibiotic can be used to select for transformed plant cells from among plant cells that are not transformed. Examples of suitable selectable markers are described above. Preferably, the marker gene is an antibiotic resistance gene whereby the appropriate antibiotic can be used to select for transformed cells from among cells that are not transformed. Examples of suitable selectable markers for use in plants include adenosine deaminase, dihydrofolate reductase, hygromycin-B-phosphotransferase, thymidine kinase, xanthine-guanine phospho-ribosyltransferase and amino-glycoside 3'-O-phosphotransferase II (kanamycin, neomycin and G418 resistance). Other suitable markers will be known to those of skill in the art Vector(s) employed in the present invention for transformation of plant cells comprise a nucleic acid sequence encoding CDR1 polypeptide, operably associated with a promoter. To effect a transformation process in accordance with the present invention, it is first necessary to construct a suitable vector and properly introduce it into the plant cell. Details of the construction of vectors utilized herein are known to those skilled in the art of plant genetic engineering.

CDR1 nucleic acid sequences utilized in the present invention can be introduced into plant cells using Ti plasmids of Agrobacterium tumefaciens, root-inducing (Ri) plasmids, and plant virus vectors. (For reviews of such techniques see, for example, Weissbach & Weissbach, *Methods for Plant Molecular Biology*, Section Vifi, pp. 421–463, Academic Press, N.Y., 1988; Grierson & Corey, *Plant Molecular Biology*, 2d Ed., Ch. 7–9, Blackie, London, 1988; and Horsch et al., *Science*, 227:1229, 1985; each incorporated herein by reference). In addition to plant transformation vectors derived from the Ti or root-inducing (Ri) plasmids of Agrobacterium, alternative methods of transformation may be utilized including the use of liposomes, electroporation, chemicals that increase free nucleic acid uptake, transformation using viruses or pollen and the use of biolistic transformation.

One of skill in the art will be able to select an appropriate vector for introducing the CDR1 polynucleotide sequence in a relatively intact state. Thus, any vector which will produce a plant carrying the introduced nucleic acid sequence should be sufficient. Even use of a naked piece of nucleic acid would be expected to confer the properties of this invention, though at low efficiency. The selection of the vector, or whether to use a vector, is typically guided by the method of transformation selected.

The transformation of plants in accordance with the invention may be carried out in essentially any of the various ways known to those skilled in the art of plant molecular biology. (See, for example, *Methods of Enzymology*, Vol. 153, Wu and Grossman, Eds., Academic Press, 1987, incorporated herein by reference). As used herein, the term "transformation" means alteration of the genotype of a host plant by the introduction of CDR1 nucleic acid sequence.

For example, an CDR1 nucleic acid sequence can be introduced into a plant cell utilizing *Agrobacterium tumefaciens* containing the Ti plasmid, as mentioned briefly above. In using an *A. tumefaciens* culture as a transformation vehicle, it is advantageous to use a nononcogenic strain of Agrobacterium as the vector carrier so that normal nononcogenic differentiation of the transformed tissues is possible. It is also preferred that the Agrobacterium harbor a binary Ti plasmid system. Such a binary system comprises 1) a first Ti plasmid having a virulence region essential for the introduction of transfer nucleic acid (T-DNA) into plants, and 2) a chimeric plasmid. The latter contains at least one border region of the T-DNA region of a wild-type Ti plasmid flanking the nucleic acid to be transferred. Binary Ti plasmid systems have been shown effective to transform plant cells (De Framond, *Biotechnology* 1:262, 1983; Hoekema et al., *Nature* 303:179, 1983). Such a binary system is preferred because it does not require integration into the Ti plasmid of Agrobacterium, which is an older methodology.

Methods involving the use of Agrobacterium in transformation according to the present invention include, but are not limited to: 1) cocultivation of Agrobacterium with cultured isolated protoplasts; 2) transformation of plant cells or tissues with Agrobacterium; or 3) transformation of seeds, apices or meristems with Agrobacterium.

In addition, gene transfer can be accomplished by in plant a transformation by Agrobacterium, as described by Bechtold et al., (CR. *Acad. Sci. Paris* 316:1 194, 1993) and exemplified in the Examples herein. This approach is based on the vacuum infiltration or dipping of a suspension of Agrobacterium cells.

The preferred method of introducing CDR1 polynucleotide into plant cells is to infect such plant cells, an explant, a meristem or a seed, with transformed *Agrobacterium tumefaciens* as described above and in the Examples. Under appropriate conditions known in the art, the transformed plant cells are grown to form shoots, roots, and develop further into plants.

Alternatively, CDR1 polynucleotide can be introduced into a plant cell using mechanical or chemical means. For example, the nucleic acid can be mechanically transferred into the plant cell by microinjection using a micropipette. Alternatively, the nucleic acid may be transferred into the plant cell by using polyethylene glycol which forms a precipitation complex with genetic material that is taken up by the cell.

CDR1 polynucleotide can also be introduced into plant cells by electroporation (From et al., *Proc. Natl. Acad. Sci. U.S.A.* 82:5824, 1985, which is incorporated herein by reference). In this technique, plant protoplasts are electroporated in the presence of vectors or nucleic acids containing the relevant nucleic acid sequences. Electrical impulses of high field strength reversibly permeabilize membranes allowing the introduction of nucleic acids. Electroporated plant protoplasts reform the cell wall, divide and form a plant callus. Selection of the transformed plant cells with the transformed gene can be accomplished using phenotypic markers as described herein.

Another method for introducing CDR1 polynucleotide into a plant cell is high velocity ballistic penetration by small particles with the nucleic acid to be introduced contained either within the matrix of such particles, or on the surface thereof (Klein et al., *Nature* 327:70, 1987). Bombardment transformation methods are also described in Sanford et al. (*Techniques* 3:3–16, 1991) and Klein et al. (*Bio/Techniques* 10:286, 1992). Although, typically, only a single introduction of a new nucleic acid sequence is required, this method particularly provides for multiple introductions.

Cauliflower mosaic virus (CaMV) may also be used as a vector for introducing nucleic acid into plant cells (U.S. Pat. No. 4,407,956). CaMV viral nucleic acid genome is inserted into a parent bacterial plasmid creating a recombinant nucleic acid molecule which can be propagated in bacteria. After cloning, the recombinant plasmid again may be cloned and further modified by introduction of the desired nucleic acid sequence (e.g., the CDR1 sequence). The modified viral portion of the recombinant plasmid is then excised from the parent bacterial plasmid, and used to inoculate the plant cells or plants.

As used herein, the term "contacting" refers to any means of introducing CDR1 into the plant cell, including chemical and physical means as described above. Preferably, contacting refers to introducing the nucleic acid or vector into plant cells (including an explant, a meristem or a seed), via *Agrobacterium tumefaciens* transformed with the CDR1 encoding nucleic acid as described above.

Normally, a transformed plant cell is regenerated to obtain a whole plant from the transformation process. The immediate product of the transformation is referred to as a "transgenote. The term "growing" or "regeneration" as used herein means growing a whole plant from a plant cell, a group of plant cells, a plant part (including seeds), or a plant piece (e.g., from a protoplast, callus, or tissue part).

Regeneration from protoplasts varies from species to species, but generally the process is initiated by first providing a suspension of protoplasts. In certain species, plant formation can be induced from the protoplast suspension, followed by ripening and germination as natural plant. The culture media will generally contain various amino acids and hormones, necessary for growth and regeneration. Examples of hormones utilized include auxins and cytokinins. It is sometimes advantageous to add glutamic acid and proline to the medium, especially for plant species such as corn and alfalfa. Efficient regeneration will depend on the medium, the genotype, and the history of the culture. If these variables are controlled, regeneration is reproducible.

Regeneration also occurs from plant callus, explants, organs or parts. Transformation can be performed in the context of organ or plant part regeneration. (see *Methods in Eyology* Vol. 118, 1987, and Klee et al., *Annual Review of Plant Physiology*, 38:467, 1987). Utilizing the leaf disk-transformation-regeneration method of Horsch et al., *Science* 272:1229, 1985, disks are cultured on selective media, followed by shoot formation in about 2–4 weeks. Shoots that develop are excised from calli and transplanted to appropriate root-inducing selective medium. Rooted plantlets are transplanted to soil as soon as possible after roots appear. The plantlets can be reported as required, until reaching maturity.

In vegetatively propagated crops, the mature transgenic plants are propagated by utilizing cuttings or tissue culture techniques to produce multiple identical plants. Selection of desirable transgenotes is made and new varieties are obtained and propagated vegetatively for commercial use.

In seed propagated crops, the mature transgenic plants is self crossed to produce a homozygous inbred plant. The resulting inbred plant produces seed containing the newly introduced foreign gene(s). These seeds can be grown to produce plants that would produce the selected phenotype, e.g., increased yield.

Parts obtained from regenerated plant, such as flowers, seeds, leaves, branches, roots, fruit, and the like are included in the invention, provided that these parts comprise cells that have been transformed as described. Progeny and variants, and mutants of the regenerated plants are also included within the scope of the invention, provided that these parts comprise the introduced nucleic acid sequences.

After selecting the transformed cells, one can confirm expression of the desired heterologous gene. Simple detection of mRNA encoded by the inserted DNA can be achieved by well known methods in the art, such as Northern blot hybridization. The inserted sequence can be identified by Southern blot hybridization, as well.

Plants exhibiting increased disease resistance as compared with wild-type plants can be selected by visual observation. (See also U.S. Pat. No. 5,530,187, incorporated herein by reference.) The invention includes plants produced by the method of the invention, as well as plant tissue and seeds.

In yet another embodiment, the invention provides a method for genetically modifying a plant cell such that a plant, produced from the cell, is characterized as having increased disease resistance as compared with a wild-type plant. The method includes introducing at least one nucleic acid sequence encoding CDR1 polypeptide into a plant cell a transformed plant cell; growing the transformed plant cell under conditions which allow expression of CDR1 polypeptide thereby producing a plant having increased disease resistance. Conditions such as environmental and promoter inducing conditions vary from species to species, but should be the same within a species.

In another embodiment, the invention provides a method of producing a plant characterized as having increased disease resistance by introducing CDR1 polynucleotide into a plant cell to obtain a transformed cell, and then growing the transformed plant cell under conditions which permit expression of CDR1 polypeptide to produce a plant with increased disease resistance. The term "expression" refers to an increase in transcription of CDR1 DNA or translation of CDR1 mRNA or activity of CDR1 polypeptide.

In yet another embodiment, the invention provides a method of producing a plant characterized by having increased disease resistance as compared to a wild type plant by contacting a susceptible plant with an CDR1 promoter-inducing amount of an agent which induces CDR1 gene expression, wherein induction of CDR1 gene expression results in production of a plant having increased disease resistance as compared to a plant not contacted with the agent. The agent can induce endogenous CDR1 gene expression, for example. In a preferred embodiment, the plant is a transgenic plant containing a nucleic acid encoding an inducible promoter operably linked to nucleic acid encoding CDR1. Examples of inducible promoters useful in plants include those induced by chemical means, such as the yeast metallothionein promoter which is activated by copper ions (Mett, et al., *Proc. Natl Acad. Sci. U.S.A.* 90:4567, 1993); In2-1 and In2-2 regulator sequences which are activated by substituted benzenesulfonamides, e.g., herbicide safeners (Hershey, et al., *Plant Mol. Biol.* 17:679, 1991); and the GRE regulatory sequences which are induced by glucocorticoids (Schena et al., *Proc. Natl. Acad. Sci. U.S.A.* 88:10421, 1991). The term promoter inducing amount refers to that amount of agent necessary to elevate CDR1 gene expression above CDR1 expression in a plant cell not contacted with the agent. For example, a transcription factor or a chemical agent may be used to elevate gene expression from CDR1 native promoter. The invention method envisions contacting cells containing endogenous CDR1 promoter or recombinantly produced CDR1 promoter.

Screen for Identifying Novel Disease Resistance Genes

The invention provides a method of identifying novel disease resistance genes related to CDR1 by probing a nucleic acid library with at least a fragment of an isolated polynucleotide encoding CDR1, and selecting those clones that hybridize with the fragment. Novel disease resistant genes, such as homologs of CDR1 are identified by any of a number of methods. The nucleotide sequence encoding a novel disease resistance gene can be isolated according to any one of a variety of methods well known to those of ordinary skill in the art. For example, DNA encoding a CDR1 homolog can be isolated from either a cDNA library or from a genomic DNA library (see, e.g., Sambrook et al., 1989. *Molecular Cloning: A Laboratory Manual*, 2nd Ed., Cold Spring Harbor Laboratory Press, Cold Spring Harbor, N.Y.). In one embodiment, a fragment of a polynucleotide encoding CDR1 may be used as a hybridization probe with a cDNA library from the target organism of interest, where low stringency conditions are used. The probe may be a large fragment, or one or more short degenerate primers. In a preferred embodiment, the probe is at least eight nucleotides in length.

Nucleic acids having sequence similarity are detected by hybridization under low stringency conditions, for example, at 50/C and 10×SSC (0.9 M saline/0.09 M sodium citrate) and remain bound when subjected to washing at 55/C in 1×SSC. Sequence identity can be determined by hybridization under more stringent conditions, for example, at 50/C or higher and 0.1×SSC (9 mM saline/0.9 mM sodium citrate). By using probes, particularly labeled probes of DNA sequences, one can isolate homologous or related genes. The source of homologous genes may be any species, e.g. plant species, primate species, particularly human; rodents, such as rats and mice, canines, felines, bovines, ovines, equines, yeast, and nematodes.

Alternatively, the DNA encoding a novel disease resistance gene can be isolated using standard polymerase chain reaction PCR) amplification of synthetic oligonucleotide primers, e.g., as described in Mullis et al., U.S. Pat. No. 4,800,159, or expression cloning methods well known in the art (see, e.g., Sambrook et al., 1989, *Molecular Cloning: A Laboratory Manual*, 2nd Ed., Cold Spring Harbor Laboratory Press, Cold Spring Harbor, N.Y.). One of skill in the art can readily design primers for PCR amplification based on the sequence of a polynucleotide encoding CDR1 polypeptide.

Between plant species, e.g monocotyledons, dicotyledons, and woody species, homologs typically have substantial sequence similarity, i.e. at least 75% sequence identity between nucleotide sequences. Sequence similarity is calculated based on a reference sequence, which may be a subset of a larger sequence, such as a conserved motif, coding region, or flanking region, for example. A reference sequence will usually be at least about 18 nucleotides (nt) long, more usually at least about 30 nt long, and may extend to the complete sequence that is being compared. Algorithms for sequence analysis are known in the art, such as BLAST, described in Altschul et al. (1990) *J. Mol. Biol.* 215:403–10. The sequences provided herein are essential for recognizing CDR1 related and homologous proteins in database searches.

Antibody, Antisense or Ribozyme Inhibition of CDR1 for Increased Disease Susceptibility In another embodiment, the invention provides a method for increasing susceptibility of a plant to disease by inhibiting expression of CDR1. For example, it may be desirable to provide a CDR1 specific antibody, as described above, or antisense oligonucleotides to a plant in order to provide a means for killing or reducing growth of the plant, e.g., weeds. The Examples indicate that CDR1 is an extracellular protein and therefore is accessible to inhibition by CDR1 antibodies. Antisense technology offers a very specific and potent means of inhibiting CDR1 expression, for example, by decreasing the amount of CDR1 expression in a cell. Antisense polynucleotides in context of the present invention includes both short sequences of DNA known as oligonucleotides of usually 10–50 bases in length as well as longer sequences of DNA that may exceed the length of the CDR1 gene sequence itself. Antisense polynucleotides useful for the present invention are complementary to specific regions of a corresponding target mRNA. Hybridization of antisense polynucleotides to their target transcripts can be highly specific as a result of complementary base pairing. The capability of antisense polynucleotides to hybridize is affected by such parameters as length, chemical modification and secondary structure of the transcript which can influence polynucleotide access to the target site. See Stein et al., *Cancer Research* 48:2659 (1988). An antisense polynucleotide can be introduced to a cell by introducing a DNA segment that codes for the polynucleotide into the cell such that the polynucleotide is made inside the cell. An antisense polynucleotide can also be introduced to a cell by adding the polynucleotide to the environment of the cell such that the cell can take up the polynucleotide directly. The latter route is preferred for the shorter polynucleotides of up to about 20 bases in length.

In selecting the preferred length for a given polynucleotide, a balance must be struck to gain the most favorable characteristics. Shorter polynucleotides such as 10-to 15-mers, while offering higher cell penetration, have lower gene specificity. In contrast, while longer polynucleotides of 20–30 bases offer better specificity, they show decreased uptake kinetics into cells. See Stein et al., PHOSPHOROTHIOATE OLIGODEOXYNUCLEOTIDE ANALOGUES in "Oligodeoxynucleotides—Antisense Inhibitors of Gene Expression" Cohen, ed. McMillan Press, London (1988). Accessibility to mRNA target sequences also is of importance and, therefore, loop-forming regions in targeted mnRNAs offer promising targets.

In this disclosure the term "polynucleotide" encompasses both oligomeric nucleic acid moieties of the type found in nature, such as the deoxynbonucleotide and ribonucleotide structures of DNA and RNA, and man-made analogues which are capable of binding to nucleic acids found in nature. The polynucleotides of the present invention can be based upon ribonucleotide or deoxyribonucleotide monomers linked by phosphodiester bonds, or by analogues linked by methyl phosphonate, phosphorothioate, or other bonds. They may also comprise monomer moieties which have altered base structures or other modifications, but which still retain the ability to bind to naturally occurring DNA and RNA structures. Such polynucleotides may be prepared by methods well-known in the art, for instance using commercially available machines and reagents available from Perlin-Elmer/Applied Biosystems (Foster City, Calif.).

Phosphodiester-linked polynucleotides are particularly susceptible to the action of nucleases in serum or inside cells, and therefore in a preferred embodiment the polynucleotides of the present invention are phosphorothioate or methyl phosphonate-linked analogues, which have been shown to be nuclease-resistant. Persons of ordinary skill in this art will be able to select other linkages for use in the invention. These modifications also may be designed to improve the cellular uptake and stability of the polynucleotides.

In another embodiment of the invention, the antisense polynucleotide is an RNA molecule produced by introducing an expression construct into the target cell. The RNA molecule thus produced is chosen to have the capability to hybridize to CDR1 mRNA. Such molecules that have this capability can inhibit translation of the CDR1 mRNA and thereby enhance susceptibility to disease in plant cells that contain the RNA molecule.

The polynucleotides which have the capability to hybridize with mRNA targets can inhibit expression of corresponding gene products by multiple mechanisms. In "translation arrest," the interaction of polynucleotides with target mRNA blocks the action of the ribosomal complex and, hence, prevents translation of the messenger RNA into protein. Haeuptle et al., Nucl. Acids. Res. 14:1427 (1986). In the case of phosphodiester or phosphorothioate DNA polynucleotides, intracellular RNase H can digest the targeted RNA sequence once it has hybridized to the DNA oligomer. Walder and Walder, Proc. Natl. Acad. Sci. USA 85:5011 (1988). As a further mechanism of action, in "transcription arrest" it appears that some polynucleotides can form "triplex," or triple-helical structures with double stranded genomic DNA containing the gene of interest, thus interfering with transcription by RNA polymerase. Giovannangeli et al., Proc. Natl. Acad. Sci. 90:10013 (1993); Ebbinghaus et al. J. Clin. Invest. 92:2433 (1993).

In one preferred embodiment, CDR1 polynucleotides are synthesized according to standard methodology. Phosphorothioate modified DNA polynucleotides typically are synthesized on automated DNA synthesizers available from a variety of manufacturers. These instruments are capable of synthesizing nanomole amounts of polynucleotides as long as 100 nucleotides. Shorter polynucleotides synthesized by modern instruments are often suitable for use without further purification. If necessary, polynucleotides may be purified by polyacrylamide gel electrophoresis or reverse phase chromatography. See Sambrook et al., MOLECULAR CLONING: A Laboratory Manual, Vol. 2, Chapter 11, Cold Spring Harbor Laboratory Press, Cold Spring Harbor, N.Y. (1989).

Alternatively, a CDR1 polynucleotide in the form of antisense RNA may be introduced to a cell by its expression within the cell from a standard DNA expression vector. CDR1 DNA antisense sequences can be cloned from standard plasmids into expression vectors, which expression vectors have characteristics permitting higher levels of, or more efficient expression of the resident polynucleotides. At a minimum, these constructs require a prokaiyotic, plant-specific or eukaryotic promoter sequence which initiates transcription of the inserted DNA sequences. A preferred expression vector is one where the expression is inducible to high levels. This is accomplished by the addition of a regulatory region which provides increased transcription of downstream sequences in the appropriate host cell. See Sambrook et al., Vol. 3, Chapter 16 (1989).

For example, CDR1 antisense expression vectors can be constructed using the polymerase chain reaction (PCR) to amplify appropriate fragments from single-stranded cDNA of a plasmid in which CDR1 cDNA has been incorporated. Fang et al., J. Biol. Chem. 267 25889–25897 (1992). Polynucleotide synthesis and purification techniques are described in Sambrook et al. and Ausubel et al. (eds.), CURRENT PROTOCOLS IN MOLECULAR BIOLOGY (Wiley Interscience 1987) (hereafter "Ausubel", respectively. The PCR procedure is performed via well-known methodology. See, for example, Ausubel, and Bangham, "The Polymerase Chain Reaction: Getting Started," in PROTOCOLS IN HUMAN MOLECULAR GENETICS (Humana Press 1991). Moreover, PCR kits can be purchased from companies such as Stratagene Cloning Systems (La Jolla, Calif.) and Invitrogen (San Diego, Calif.).

Antisense polynucleotides according to the present invention are derived from any portion of the open reading frame of the CDR1 cDNA. Preferably, mRNA sequences (i) surrounding the translation initiation site and (ii) forming loop structures are targeted. Based upon the size of the human genome, statistical studies show that a DNA segment approximately 14–15 base pairs long will have a unique sequence in the genome. To ensure specificity of targeting CDR1 RNA, therefore, it is preferred that the antisense polynucleotides are at least 15 nucleotides in length. Thus, the shortest polynucleotides contemplated by the present invention encompass nucleotides corresponding to positions 1–14, 1–15, 1–16, 1–17, 1–18, 1–19, 2–16, 3–17, etc. of the CDR1 cDNA sequence. Position 1 refers to the first nucleotide of the CDR1 coding region. In Example 9, an antisense derived from the entire CDR1 gene was utilized for inhibiting CDR1 expression, thereby increasing susceptibility to disease in a transgenic plant.

Not every antisense polynucleotide will provide a sufficient degree of inhibition or a sufficient level of specificity for the CDR1 target. Thus, it will be necessary to screen polynucleotides to determine which have the proper antisense characteristics. A preferred method to assay for a useful antisense polynucleotide is to infect a plant receiving the antisense construct with a disease causing organism, as in Example 9, and determining the susceptibility of the plant to disease.

The above disclosure generally describes the present invention. A more complete understanding can be obtained by reference to the following specific examples which are provided herein for purposes of illustration only and are not intended to limit the scope of the invention.

EXAMPLE 1

GENERATION OF T-DNA ACTIVATION TAGGED MUTANTS

The activation tagging binary vector pSKI15 is shown in FIG. 1. This vector is derived from pPCVICEn4HPT (Walden et al., 1994, Plant Molec. Bio. 26:152, incorporated by reference). The vector has a BAR gene as a plant selection marker which allows selection of transformants in soil. Four copies of transcriptional enhancers derived from the cauliflower mosaic virus 35S RNA promoter (4×35S enhancer) are located next to the right border sequence of the T-DNA, insertion of which into the plant genome is expected to cause strong ectopic or over-expression of adjacent plant genes. The T-DNA also contained pBluescript sequences, allowing isolation of tagged plant genes by plasmid rescue. Arabidopisis plants (ecotype Columbia) were directly transformed by agrobacterium strain GV3101 harboing pSKIl 5. Seeds harvested from the T0 plants were pooled and sown on soil. The seedlings were sprayed with herbicide Basta to select for transformants. On average, approximately 1% transformation efficiency was achieved. The Basta resistant seedlings (T1 plants) were transplanted individually and grown for four weeks before mutant screening.

EXAMPLE 2

IDENTIFICATION OF CDR MUTANTS

To screen for dominant mutants which exhibited enhanced disease resistance, four week-old T1 transgenic individuals were sprayed with 3–4×10$^8$cfu/ml virulent *Pseudomonas syringe pv. tomato*(Pst) or *P. syringae pv. maculicola* (Psm). Phenotypes were scored 4 to 7 days post infection. The individuals which exhibited no disease symptoms or less severe symptoms were identified as putative mutants. As the screening was performed in the T1 generation, such identified mutants are presumably dominant, most likely gain-of-function mutation(s) resulting from activation of corresponding genes driven by the 35S enhancers. These mutants were named cdr (constitutive disease resistance).

Approximately five thousand of the activation tagged lines were screened for cdr mutants and 12 putative cdr mutants were identified. The selfed progenies (T2 plants) of these putative cdr mutants were rescreened by infection with either Psm or Pst. cdr1-D was a confirmed mutant and is further described herein.

cdr1-D was originally identified by its resistance to Pst. Neighboring plants were severely infected following spraying with Pst, whereas the cdr plant was almost completely asymptomatic. cdr1-D plants were dwarf and the leaves were slightly curled and darker. No abnormality was observed in shoot and flower development, and cdr1-D plants exhibited normal seed setting.

Genetic Analysis of cdr1-D Allele

Among 241 T2 plants, 176 were dwarf and Basta resistant, 28 wild-type looking and Basta resistant, and 37 wild-type looking and Basta susceptible. No dwarf, Basta susceptible progeny were found. Among over 60 dwarf T2 plants so far tested, all exhibited enhanced disease resistance, and none of over 20 wild-type-looking plants tested showed enhanced disease resistance. Therefore, no recombination between cdr1-D mutation dwarf stature, and Basta resistance was detected among over 80 T2 progeny scored. This result strongly suggests that the cdr1-D mutation is caused by T-DNA insertion and the dwarf stature is likely a side effect of constitutive expression of disease resistance mechanisms mediated by the cdr1-D mutation. The segregation data demonstrated that the cdr1-D mutation is dominant to its wild-type allele. The progeny from a backcross between wild-type Columbia and the cdr1-D T1 plant (heterozygous) segregated 1:1 for cdr1-D and wild-type plants, indicating that the cdr1-D mutation is dominant. In addition, the F2 segregation data also suggested that the cdr1-D T1 plant contains two T-DNA insertions which are lined with a genetic distance of 39 cM. Only one insertion was associated with the cdr1-D mutation. Southern analysis further demonstrated that the cdr1-D T1 plants contains two T-DNA insertions (see below).

EXAMPLE3 cdr1-D IS RESISTANT TO BOTH Pst AND Psm

Resistance to Pst in cdr1-D and wild-type plants was further monitored by measuring bacterial growth in the plants using a dipping infection procedure (see below). In wild-type plants, the pathogen growth was over 10,000 fold above inoculation levels after 4 days. However, in the cdr1-D mutants, pathogen growth increased 200 fold. The resistance of cdr1-D plants to Psm was also examined. Following infection with Psm, the cdr1-D plants were found to be symptomless.

EXAMPLE 4

ACTIVATION OF DEFENSE-RELATED GENES IN THE cdr1-D MUTANT

In response to pathogen attack, plants activate a battery of defense-related genes in the infected site as well as in tissues distant from the infection sites. Such genes include PR genes encoding pathogenesis-related proteins, such as PAL1, which encodes phenylalanine ammonia lyase, and GST encoding glutathione S-transferase. Other mutants which constitutively express disease resistance accumulate high levels of defense-related genes. To study if the defense-related genes are constitutively expressed in the cdr1-D mutants, the steady-state levels of PR1, PR2, PAL1, GST1, and rbohA transcripts were examined. The basal levels of PR1 and PR2 transcripts in the cdr1-D mutants were approximately 200-fold higher relative to those in healthy wild-type plants. The cdr1-D mutant plants also accumulated at least 20 times more rbohA transcripts than the wild-type plants do. However, the GST1 transcript level in the mutant plants was only 2–3 fold higher than in wild-type plants. In addition, gene expression was suppressed in cdr1-D mutant plants.

Defensin genes are also activated following pathogen attach or jasmonate application. Their activation is apparently independent of salicylic acid- PDF1.2, an Arabidopsis gene encoding a defensin protein, is constitutively activated in cdr5 and cdr6 mutants. However, the level PDF1.2 transcripts was not elevated in the cdr1-D plants.

EXAMPLE 5 cdr1-D EXHIBITS ELEVATED LEVELS OF SALICYLIC ACID (SA) AND SALICYLIC ACID GLUCOSIDE (SAG)

Salicyclic acid (SA) plays important roles in the primary resistance response to pathogen infection as well as in the induction of systemic acquired resistance. Elevated levels of SA and SA -glucoside (SAG), a sugar-conjugated form of SA, have been found to be associated with some previously reported constitutive disease resistant mutants. Table 2 shows that the levels of SA and SAG in the cdr1-D mutants SA and SAG were approximately 15 and 35 times higher, respectively, than the levels found in wild-type plants.

Salicylic Acid is Required for cdr1-D Mediated Disease Resistance

To examine the relationship between the cdr1-D mutant phenotype and salicylic acid, cdr1-D plants were crossed to the plants expressing the bacterial nahG gene. The nahG gene encodes salicylate hydroxylase which converts salicylic acid to catechol, thereby preventing salicylic acid accumulation. nahG plants were used as female parents and cdr1-D plants as male parents. The F1 plants were selected for resistance to Basta. Although cdr1-D nahG F1 plants were more compact, and the leaves where slightly rippled, the cdr1-D dwarf stature was suppressed in the F1 plants.

The suppression of defense gene activation was examined in the cdr1-D nahG plants. In contrast to the cdr1-D mutants, the cdr1-D nahG plants did not exhibit elevated levels of PR1 and PR2 transcripts. Furthermore, the cdr1-D nahG plants no longer exhibited enhanced resistance to the virulent Pst. The in planta bacterial growth measurement following hand infiltration procedure also demonstrated that the cdr1-D mediated resistance was completely suppressed in the cdr1-D nahG F1 plants.

The data revealed that nahG suppressed cdr1-D mediated defense gene activation, enhanced disease resistance, as well as the dwarf stature, demonstrating that SA is a necessary component in cdr1-D mediated disease resistance pathway.

EXAMPLE 6

A DOMINANT SUPPRESSER OF cdr1-D MEDIATED SIGNALING PATHWAY IN ARABIDOPSIS ECOTYPE Landsberg erecta (Ler)

cdr1-D develops spontaneous micro-oxidative bursts and micro-lesions The high level of rbohA expression suggested that the mutant might generate high levels of reactive oxygen species. To examine this, DAB staining was used for in vivo and in situ detection of H2O2. DAB polymerizes instantly and locally as soon as it comes into contact with H2O2. DAB polymers exhibit a reddish-brown color. Interestingly, in the uninfected cdr1-D leaves, some cells are generating high levels of H2O2.

Most constitutive disease resistance mutants develop visible spontaneous lesions. The cdr1-D mutant does not exhibit obvious lesions. However, with the Trypan Blue staining technique, small lesions were observed in the mutant leaves.

EXAMPLE 7

CLONING AND ANALYSIS OF CDR1 GENE

Consistent with the segregation data indicating that the T1 cdr1-D plant contained at least two T-DNA insertions, DNA gel blot analyses detected two genomic fragments containing 35S enhancer sequence in the EcoRI-digested genomic DNA isolated from pooled self-progeny of the cdr1-D T1 plant. The 5 kb EcoRI fragment was present in both Basta resistant wild-type progeny and cdr1-D plants, whereas the 10 kb fragment cosegregated with the cdr1-D allele. cdr1-D lines which only contain the 10kb 35S enhancer-hybridization fragment were isolated. The 10 kb 35S enhancer-containing EcoRI fragments was isolated using plasmid rescue (see below). The rescued plasmid was named pCDR1E. Sequence and restriction digestion analysis of PCDR1E reveal that it contained approximately 4.5 kb of plant sequence.

The entire 4.5 kb plant sequence was used as a probe in Northern analyses. A single strong band of 1.5–1.6 kb transcript was detected in the cdr1 mutant plants but was not detectable in wild-type plants. No other transcript was detected in either the wildtype plants or the cdr1-D plants. The 1.6 kb transcript represented the coding sequence of the candidate CDR1 gene.

The 4.5 kb plant sequence of pCDR1E was used to screen approximately $4 \times 10^5$ plaques from a cDNA library (CD4–7) and $1 \times 10^5$ plaques from another size-fractionated (1–2 kb fraction) cDNA library (CD). Two cDNA clones (PCDR1 C1 and pCDR1C2) from the latter library were identified. Sequence analysis indicated that both cDNA clones were derived from the same gene. The cDNA insert in pCDR1C1 was 1485 bp in length without a polyA tail, and was found to be 64 bp longer than that in pCDR1C2.

pCDR1 E and pCDR1 C1 were fully sequenced and their organization is presented in FIG. 2. The cDNA is derived from the genomic region 0.8kb downstream of the 35S enhancers (see FIG. 3). No intron was present.

The XbaI fragment from pCDR1E, which includes one copy of the 35S enhancer and the candidate CDR1 gene, was subcloned into the binary vector pBI101 to generate the pBI/CDR1X construct. When transformed into wild-type plants, this fragment was found to cause similar phenotypes as seen in the original cdr1-D mutant, confirming that the cloned sequence is indeed the CDR1 gene.

EXAMPLE 8

SEQUENCE, ANALYSIS OF CDR1 PROTEIN

The CDR1 gene contained an open reading frame that encoded a 437-amino acid polypeptide with a predicated molecular mass of 47 kDa (FIG. 3). The deduced protein was predicated by the PSORT algorithm (Nakai and Kanehisa, 1992) to be extracellular, with a signal pepetide cleaved at position 25.

A BLAST (Altschul et al., 1990, *J. Mol. Biol.* 215:403–410) search of the GenBank databases revealed that CDR1 shared significant sequence homology with aspartic proteases. Like most of the aspartic proteases identified so far from a variety of organisms, CDR1 consists of two aspartic protease domains. The most homologous sequence in the databases is an Arabidopsis genomic sequence (GenBank accession # AC006193, from sequence 4600 to 55982) with an unknown function identified from Arabidopsis genome sequencing projects. This sequence shares 71% sequence identity to CDR1 at the amino acid level. Database searches also indicated that the Arabidopsis genome contains at least 14 genes that share significant sequence similarity with CDR1.

EXAMPLE 9

ANTISENSE SUPPRESSION OF CDR1 GENE CAUSES ENHANCED DISEASE SUSCEPTIBILITY

The full-length cDNA of the CDR1 gene was fused to the 35S promoter in the antisense orientation. The antisense construct was transferred into wild-type Arabidopsis (Columbia ecotype). Twelve independent T1 transgenics were infected with a virulent Psm avrRpm1. One of the transgenic lines (Anti-12-1) exhibited susceptibility to the infection.

EXAMPLE 10

TRANSIENT INDUCTION OF THE CDR1 GENE BY A CHEMICAL INDUCES LOCAL AND SYSTEMIC DISEASE RESISTANCE RESPONSES

The CDR1 cDNA was subcloned into a glucocorticoid-mediated transcriptional induction system to generate pTA-CDR1, in which CDR1 expression is under control of the glucocorticoid-inducible promoter. To induce the CDR1 gene, the plants were sprayed with Dexamethazone (Dex), a synthetic hormone. Induction of CDR1 gene expression was detected within three hours after Dex application and reached its highest level in two days. The induction of the CDR1 gene quickly switched on expression of PR2 and PR1 genes. Local induction of CDR1 by hand infiltration of Dex was found to induce PR1 and PR2 expression in the systemic leaves.

To examine if the transient induction of CDR1 can enhance resistance to pathogen infection, the TA-CDR1 transgenic plants and control plants (carrying the pTA vector sequence only) were infected by spraying with Pst suspension two days after the plants were treated with Dex. The TA-CDR1 transgenics exhibited enhanced resistance to the infection. Local induction of the CDR1 gene also made the whole plants more resistant to the infection.

EXAMPLE 11

CDR1 IS AN EXTRA-CELLULAR PROTEIN

Anti-CDR1 polyclonal antibodies were raised against a synthetic peptide derived from the near C-terminus of the deduced CDR1 protein. The crude antibodies were then affinity-purified using the recombinant CDR1 protein expressed in *E. coli*. The purified antibodies detected a single polypeptide with an approximate size of 58 kDa in CDR1 over-expressing plants, including the cdr1-D and the Dex-induced TA-CDR1 plants. The abundance of CDR1 protein in wild-type plants is presumably too low to be detected by the antibodies. The size of the detected CDR1 protein is bigger than the predicted size of the intact CDR1 protein (47 kDa), indicating that the mature CDR1 protein is modified.

The CDR1 protein is predicted to be extra-cellular. To test this, intercellular fluids (IFs) were isolated from the CDR1-overexpressing plants and from control plants. The abundance of CDR1 protein in the IFs detected by the antibodies was at least 10–15 fold higher than in the total crude extracts, demonstrating that the CDR1 protein is localized in intercellular spaces.

EXAMPLE 12

INTERCELLULAR FLUIDS FROM CDR1-OVEREXPRESSING ARABIDOPSIS INDUCE PR GENE EXPRESSION LOCALLY AND SYSTEMICALLY

When hand-infiltrated into wild-type leaves, the IFs isolated from the cdr1-D and Dex-induced TA-CDR1 plants were found to strongly induce PR1 and PR2 gene expression. To further determine the molecular features of the elicitor activity that is inducing PR proteins, the IFs were size fractionated by using a 10 kDa molecular weight cut-off filter. The higher (>10 kf)a) molecular weight fraction (HMWF) was found to account for the major elicitor activity seen in the crude IFs. The HMWF also induced PR gene expression in the secondary leaves. The lower molecular weight fraction (LMWF) was found to weakly induce PR gene expression in the primary leaves. Interestingly, the LMWF was able to induce PR gene expression in the secondary leaves as effectively as the HMWF. Further size fractionation by using a 3 kDa molecular weight cut-off filter demonstrated that the elicitor activity in the LMWF has a size of 3–10 kDa.

EXAMPLE 13

CDR1 RELEASES A 4.5 KDA POLYPEPTIDE IN INTERCELLULAR FLUIDS

Figure 4A:
FIG. 4 is a 1-D silver-stained gel showing a 4.5 kDa polypeptide induced by CDR1.
Figure 4B:
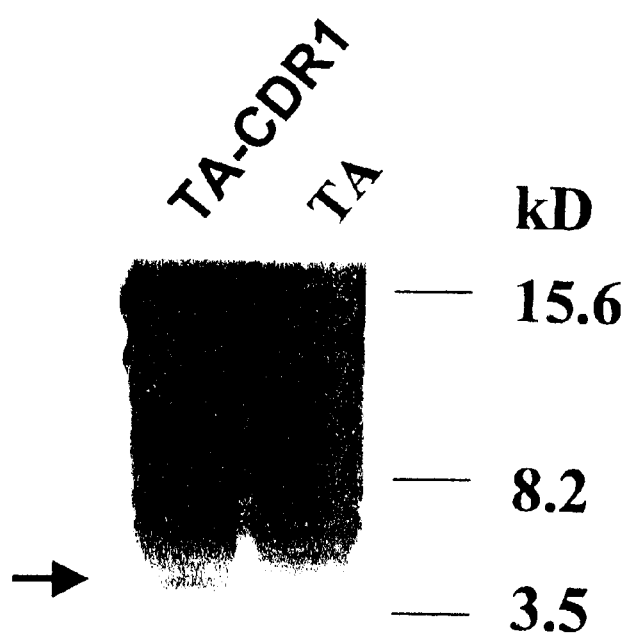

The IFs were concentrated using a 3 kDa molecular weight cut-off filter. The concentrated IFs were separated on a 1D PAGE gel and silver-stained. An approximately 4.5 kDa polypeptide accumulated only in the IFs isolated from CDR1-induced plants (FIG. 4). This CDR1-released polypeptide could have the elicitor activity that induces local and systemic disease resistance responses.

EXAMPLE-14

MATERIALS AND METHODS

1. Plant Materials

Arabidopsis thaliana ecotype Columbia that were used for transformation were grown at 23 C under short-day light period (9 h of light and 15 h of dark) for 30 days, followed by growth under long-day conditions until mature.

Arabidopsis plants were transformed as previously described using an agrobacterium strain GV3101 pMP90RK harboring activation tagging vector pSKI15 (FIG. 1) which has BAR gene for selection with Basta. The T1 seeds were planted in soil and the seedlings were sprayed with Basta to select for transformants. The Basta resistant seedlings were transplanted and grown under short-day conditions for approximately 4 weeks before being screened for enhanced disease resistance mutants.

2. Pathogens and Mutant Screening

*Pseudomonas syringe pv. Tomato* (Pst) and *P. Syringe pv. Maculicola* were obtained from and grown as described. Bacteria were pelleted from an overnight culture and resuspended in water to a concentration of $2-4 \times 10^8$ cfu/ml. The detergent Silwet-L77 was added to a final concentration of 0.02%. Plants were sprayed with the bacterial suspension using a hand spraying bottle and then covered for 24 hours to maintain high humidity. Symptoms were scored 4–7 days post infection. The putative mutants were transplanted and grown under long-day conditions to maturity.

3. Isolation and Analysis of Arabidopsis Nucleic Acids

Arabidopsis genomic DNA was isolated using a modified cetyltrimethylammounia bromide (CTAB) procedure (Saghai-Maroff et al., 1984). Total RNA was isolated from aerial parts of 4–5 weeks old plants which had not started to bolt. Labeling of DNA fragments with phosphorous-32, electrophoresis, blotting of nucleic acids, and hybridization were conducted according to standard procedures (Sambrook, Molecular Cloning, A Laboratory Manual, Cold Spring Harbor Laboratory Press).

4. Cloning of T-DNA Flanking Plant Sequence

To clone the plant sequence flanking the T-DNA borders, a plasmid rescue approach was conducted. Briefly, approximately 2ug of genomic DNA was digested with KpnI or EcoRI and then purified by extraction once with 1:1 phenol:chloroform, following by ethonol precipitation. The purified DNA fragments were ligated in a total volume of 200 ul reaction for overnight. The ligation reaction was extracted once with phenol:chloroform (1:1), precipatated with ethonal and resuspended in 10 ul distilled water. 1 ul of the purified ligation reaction was used to transform *E. Coli* using the electroporation procedure as previously described (Sambrook et al., 1989, supra).

5. Cloning of Genomic Clones and cDNA Clones

An arabidopsis genornic library derived from Ler ecotype (Voytas et al., 1990) and two cDNA libraries derived from ecotype Colombia were screened according to standard procedures (Sambrook et al., 1989, supra).

6. Antibody Production and Purification and Immunoblot Analysis

A peptide of 14 amino acids, DTVSKTVSFKPTDC, was synthesized and injected into rabbits to raise polyclonal antibodies. The resulting antisera were affinity purified using the CDR1 fusion protein immobilized on nitrocellulose filters as described (Sambrook et al., 1989).

Protein separation and immunoblotting procedures were conducted according to standard procedures (Sambrook et al., 1989).

7. Isolation of Intercellular Fluids

Leaves were cut into 0.2–0.5cm wide slices and rinsed with water. The leaf slices were immersed in water, vacuum-infiltrated for 5–10 min, blotted dry, and placed into the barrel of a 20 or 30 ml syringe. The syringe was placed in an appropriate size centrifuge tube and centrifuged at 800g for 10 min. The intercellular fluids were collected at the bottom of the tube.

It is to be understood that while the invention has been described in conjunction with the detailed description thereof, that the foregoing description is intended to illustrate and not limit the scope of the invention, which is defined by the scope of the appended claims. Other aspects, advantages, and modifications are within the scope of the following claims.

What is claimed is:

1. An isolated polynucleotide comprising the sequence set forth in SEQ ID NO:1.

2. An isolated polynucleotide encoding an amino acid sequence as set forth in SEQ ID NO:2.

3. An isolated polynucleotide encoding a constitutive disease resistance 1 (CDR1) polypeptide, wherein said polynucleotide hybridizes to a nucleic acid sequence which is fully complementary to SEQ ID NO:1, or the full-length complement of SEO ID NO:1, under high stringency conditions of 0.1×SSC at 68° C.

4. The polynucleotide of claim 1, wherein the polynucleotide is isolated from a plant cell.

5. The polynucleotide of claim 2, wherein said polynucleotide is operatively linked to an expression control sequence.

6. The polynucleotide of claim 5, wherein the expression control sequence is a promoter.

7. The polynucleotide of claim 6, wherein the promoter is tissue specific.

8. An expression vector comprising the polynucleotide of claim 2.

9. The vector of claim 8, further comprising a DNA sequence encoding a selectable marker.

10. The vector of claim 9, wherein said selectable marker confers antibiotic resistance.

11. The vector of claim 8, wherein the vector is a viral vector.

12. The vector of claim 8, wherein the vector is a plasmid.

13. The vector of claim 12, wherein the plasmid is a Ti plasmid of *Agrobacterium tumefaciens*.

14. The vector of claim 12, wherein the plasmid is an Ri plasmid of *Agrobacterium rhizogenes*.

15. A host cell comprising the vector of claim 8.

16. An isolated polynucleotide, wherein said isolated polynucleotide has a sequence that is at least 75% identical to the sequence of SEQ ID NO:1, and wherein said polynucleotide encodes a constitutive disease resistance (CDR1) polypeptide.

17. The isolated polynucleotide of claim 16, wherein the polynucleotide is operatively linked to an expression control sequence.

18. The isolated polynucleotide of claim 17, wherein the expression control sequence is a promoter.

19. The polynucleotide of claim 18, wherein the promoter is tissue specific.

20. An expression vector comprising the polynucleotide of claim 16.

21. The expression vector of claim 20, further comprising a DNA sequence encoding a selectable marker.

22. The expression vector of claim 21, wherein said selectable marker confers antibiotic resistance.

23. The expression vector of claim 20, wherein the vector is a viral vector.

24. The expression vector of claim 20, wherein the vector is a plasmid.

25. The expression vector of claim 24, wherein the plasmid is a Ti plasmid of *Agrobacterium tumefaciens*.

26. The expression vector of claim 24, wherein the plasmid is an Ri plasmid of *Agrobacterium rhizogenes*.

* * * * *